(12) United States Patent
Schafer et al.

(10) Patent No.: US 9,387,195 B2
(45) Date of Patent: Jul. 12, 2016

(54) METHODS FOR TREATING DISEASES USING ISOINDOLINE COMPOUNDS

(75) Inventors: Peter H. Schafer, Belle Mead, NJ (US); Sai Shankar, Chesterfield, NJ (US)

(73) Assignee: Celgene Corporation, Summit, NJ (US)

( * ) Notice: Subject to any disclaimer, the term of this patent is extended or adjusted under 35 U.S.C. 154(b) by 112 days.

(21) Appl. No.: 14/003,750

(22) PCT Filed: Mar. 2, 2012

(86) PCT No.: PCT/US2012/027368
§ 371 (c)(1),
(2), (4) Date: Feb. 19, 2014

(87) PCT Pub. No.: WO2012/121988
PCT Pub. Date: Sep. 13, 2012

(65) Prior Publication Data
US 2014/0187599 A1 Jul. 3, 2014

Related U.S. Application Data

(60) Provisional application No. 61/449,716, filed on Mar. 7, 2011.

(51) Int. Cl.
| | | |
|---|---|---|
| A61K 31/4035 | (2006.01) | |
| A61K 9/00 | (2006.01) | |
| A61K 9/20 | (2006.01) | |
| A61K 31/5575 | (2006.01) | |
| A61K 45/06 | (2006.01) | |
| A61K 47/38 | (2006.01) | |
| A61K 47/06 | (2006.01) | |
| A61K 47/10 | (2006.01) | |
| A61K 47/14 | (2006.01) | |
| A61K 47/26 | (2006.01) | |
| A61K 9/06 | (2006.01) | |
| A61K 9/48 | (2006.01) | |
| A61K 9/70 | (2006.01) | |

(52) U.S. Cl.
CPC ........... *A61K 31/4035* (2013.01); *A61K 9/0014* (2013.01); *A61K 9/0019* (2013.01); *A61K 9/0053* (2013.01); *A61K 9/0056* (2013.01); *A61K 9/06* (2013.01); *A61K 9/2013* (2013.01); *A61K 9/2018* (2013.01); *A61K 9/2031* (2013.01); *A61K 9/2059* (2013.01); *A61K 9/2063* (2013.01); *A61K 9/4866* (2013.01); *A61K 9/7015* (2013.01); *A61K 31/5575* (2013.01); *A61K 45/06* (2013.01); *A61K 47/06* (2013.01); *A61K 47/10* (2013.01); *A61K 47/14* (2013.01); *A61K 47/26* (2013.01); *A61K 47/38* (2013.01)

(58) Field of Classification Search
CPC .................................................. A61K 31/4035
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 6,020,358 A | 2/2000 | Muller et al. | |
| 6,667,316 B1 | 12/2003 | Man et al. | |
| 6,962,940 B2 | 11/2005 | Muller et al. | |
| 2007/0259009 A1* | 11/2007 | Linder | 424/400 |
| 2008/0234359 A1 | 9/2008 | Muller et al. | |

FOREIGN PATENT DOCUMENTS

| | | |
|---|---|---|
| WO | 01/34606 A1 | 5/2001 |
| WO | 03/080049 A1 | 10/2003 |
| WO | 03/099334 A1 | 12/2003 |
| WO | 2004/009776 A2 | 1/2004 |
| WO | 2004/029040 A1 | 4/2004 |
| WO | 2005/112918 A1 | 12/2005 |
| WO | 2006/065814 A1 | 6/2006 |
| WO | 2007/079182 A1 | 7/2007 |
| WO | 2008/125111 A1 | 10/2008 |
| WO | 2009/120167 A1 | 10/2009 |
| WO | 2010/069322 A1 | 6/2010 |
| WO | 2010/091894 A2 | 8/2010 |
| WO | 2011/001212 A1 | 1/2011 |
| WO | 2011/059931 A2 | 5/2011 |

OTHER PUBLICATIONS

Gottlieb et al. Current Medical Research and Opinion, 2008, vol. 24, No. 5, pp. 1529-1538.*

(Continued)

*Primary Examiner* — James D Anderson
(74) *Attorney, Agent, or Firm* — Jones Day

(57) ABSTRACT

Methods of treating a disease selected from dermatomyositis, prurigo nodularis, pyoderma gangrenosum, alopecia areata, hidradenitis suppurtiva, rosacea, lichen planus, giant cell arteritis, Sjogren's syndrome, gout, chronic prostatitis, posterior uveitis, vulvodynia and interstitial cystitis in a human are disclosed. Specific methods encompass the administration of (+)-2-[1-(3-ethoxy-4-methoxyphenyl)-2-methylsulfonylethyl]-4-acetylaminoisoindoline-1,3-dione, cyclopropyl {2-[(1S)-1-(3-ethoxy-4-methoxyphenyl)-2-(methylsulfonyl)ethyl]-3-oxoisoindolin-4-yl}carboxamide or a combination thereof, or a pharmaceutically acceptable prodrug, metabolite, polymorph, salt, solvate or clathrate thereof.

19 Claims, 8 Drawing Sheets

(56) References Cited

OTHER PUBLICATIONS

Baughman et al., "Release of tumor necrosis factor by alveolar macrophages of patients iwth sarcoidosis," J. Lab. Clin. Med. 115:36-42 (1990).

Bissonnette et al., "Pulmonary inflammation and fibrosis in a murine model of asbestosis and silicosis. Possible role of tumor necrosis factor," Inflammation 13:329-339 (1989).

Carstensen, Drug Stability: Principles & Practices, Second Edition, Marcel Dekker, New York, NY, pp. 379-380 (1995).

Elliot et al., "TNF alpha blockade in rheumatoid arthritis: rationale, clinical outcomes and mechanisms of action," Int. J. Immunopharmacol., 17:141-145 (1995).

Dubchak et al., "New and improved strategies for the treatment of gout," Int. J Nephrology Renovascular Dis., 3:145-166 (2010).

Lowe et al., "Patent evaluation: novel dioxolanes as cholesterol lowering agents," Exp. Opin. Ther. Patents, 2(8):1309-1310 (1992).

Piguet et al., "Requirement of tumour necrosis factor for development of silica-induced pulmonary fibrosis," Nature, 344:245-247 (1990).

Van Dullemen et al., "Treatment of Crohn's disease with anti-tumor necrosis factor chimeric monoclonal antibody (cA2)," Gastroenterology, 109:129-135 (1995).

Wilen et al., "Strategies in optical resolutions," Tetrahedron, 33:2725-2736 (1977).

Wilen, Tables of Resolving Agents and Optical Resolutions, (E.L. Eliel, Ed.), University of Notre Dame Press, Notre Dame, IN, p. 268 (1972).

Wolff ed., Burger's Medicinal Chemistry and Drug Discovery, 5th Edition, John Wiley & Sons, Inc., pp. 172-178, 949-982 (1995).

\* cited by examiner

METHODS FOR TREATING DISEASES USING ISOINDOLINE COMPOUNDS

1. CROSS-REFERENCE TO RELATED APPLICATIONS

This application is a 371 of International Application No. PCT/US2012/027368, filed Mar. 2, 2012, which claims priority to U.S. provisional application no. 61/449,716, filed Mar. 7, 2011, the entirety of each of which is incorporated herein by reference.

2. FIELD OF THE INVENTION

Provided herein are methods of treating, preventing and/or managing a disease selected from dermatomyositis, prurigo nodularis, pyoderma gangrenosum, alopecia areata, hidradenitis suppurtiva, rosacea, lichen planus, giant cell arteritis, Sjogren's syndrome, gout, chronic prostatitis, posterior uveitis, vulvodynia and interstitial cystitis by the administration of (+)-2-[1-(3-ethoxy-4-methoxyphenyl)-2-methylsulfonylethyl]-4-acetylaminoisoindoline-1,3-dione, cyclopropyl{2-[(1S)-1-(3-ethoxy-4-methoxyphenyl)-2-(methylsulfonyl)ethyl]-3-oxoisoindolin-4-yl}carboxamide or a combination thereof.

Also provided herein are pharmaceutical compositions and dosage forms comprising (+)-2-[1-(3-ethoxy-4-methoxyphenyl)-2-methylsulfonylethyl]-4-acetylaminoisoindoline-1,3-dione, cyclopropyl{2-[(1S)-1-(3-ethoxy-4-methoxyphenyl)-2-(methylsulfonyl)ethyl]-3-oxoisoindolin-4-yl}carboxamide or a combination thereof for use in methods for treating, preventing and/or managing a disease selected from dermatomyositis, prurigo nodularis, pyoderma gangrenosum, alopecia areata, hidradenitis suppurtiva, rosacea, lichen planus, giant cell arteritis, Sjogren's syndrome, gout, chronic prostatitis, posterior uveitis, vulvodynia and interstitial cystitis.

3. BACKGROUND OF THE INVENTION

Tumor necrosis factor alpha (TNF-$\alpha$) is a cytokine that is released primarily by mononuclear phagocytes in response to immunostimulators. TNF-$\alpha$ is capable of enhancing most cellular processes, such as differentiation, recruitment, proliferation, and proteolytic degradation. At low levels, TNF-$\alpha$ may confer protection against infective agents, tumors, and tissue damage. However, TNF-$\alpha$ also may have a role in many diseases. For example, when administered to mammals or humans, TNF-$\alpha$ causes or aggravates inflammation, fever, cardiovascular effects, hemorrhage, coagulation, and acute phase responses similar to those seen during acute infections and shock states.

Enhanced or unregulated TNF-$\alpha$ production has been implicated in inflammatory diseases, autoimmune diseases and related diseases. Some non-limiting examples of inflammatory and autoimmune diseases include chronic pulmonary inflammatory diseases; dermatitis; psoriasis; systemic lupus erythrematosus; arthritic conditions such as rheumatoid arthritis and osteoarthritis; osteoporosis; Crohn's disease; ulcerative colitis; inflammatory-bowel disease; and multiple sclerosis. Pignet et al., 1990, *Nature*, 344:245-247, Bissonnette et al., 1989, *Inflammation* 13:329-339 and Baughman et al., 1990, *J. Lab. Clin. Med.* 115:36-42 (chronic pulmonary inflammatory diseases); Elliot et al., 1995, *Int. J. Pharmac.* 17:141-145 (rheumatoid arthritis); von Dullemen et al., 1995, *Gastroenterology*, 109:129-135 (Crohn's disease).

PDE4 is one of the major phosphodiesterase isoenzymes found in human myeloid and lymphoid lineage cells. The enzyme plays a crucial part in regulating cellular activity by degrading the ubiquitous second messenger cyclic adenosine monophosphate (cAMP) and maintaining it at low intracellular levels. Without being limited by theory, PDE4 inhibitors block the degradation of cAMP via inhibition of the phosphodiesterase type IV (PDE4) enzyme, resulting in an increase in cAMP in PDE4-expressing cells including monocytes, T cells, and neutrophils. Furthermore, the resulted increase in cAMP levels may lead to the modulation of LPS induced cytokines, including inhibition of TNF-$\alpha$ production in monocytes as well as in lymphocytes.

Pharmaceutical compounds that can block the activity or inhibit the production of certain cytokines (e.g., TNF-$\alpha$) and phosphodiesterase 4 (i.e., PDE4) may be effective in treating, preventing and/or managing inflammatory diseases, autoimmune diseases and related diseases. For example, many small-molecule inhibitors have demonstrated an ability to treat, prevent and/or managing inflammatory diseases implicated by TNF-$\alpha$ (for a review, see Lowe, 1998 *Exp. Opin. Ther. Patents* 8:1309-1332). However, there are still needs for novel drugs with improved efficacy and/or less side effects for treating inflammatory diseases, autoimmune diseases and related diseases such as dermatomyositis, prurigo nodularis, pyoderma gangrenosum, alopecia areata, hidradenitis suppurtiva, rosacea, lichen planus, giant cell arteritis, Sjogren's syndrome, gout, chronic prostatitis, posterior uveitis, vulvodynia and interstitial cystitis.

4. SUMMARY

In one aspect, provided herein are methods of treating, preventing and/or managing a disease selected from inflammatory diseases, autoimmune diseases and other related diseases such as dermatological diseases and rheumatic diseases in humans. In some embodiments, provided herein are methods of treating, preventing and/or managing a disease selected from dermatological diseases, rheumatic diseases and inflammatory diseases in human with a TNF-$\alpha$ inhibitor, a PDE4 inhibitor or a combination thereof.

As used herein and unless otherwise indicated, the terms "TNF-$\alpha$ inhibitor" and "PDE4 inhibitor" encompass small molecule drugs, e.g., small organic molecules, which are not peptides, proteins, nucleic acids, oligosaccharides or other macromolecules, that inhibit the production of TNF-$\alpha$, PDE4 or a combination thereof. In some embodiments, the compounds inhibit TNF-$\alpha$ production. In certain embodiments, the compounds may also have a modest inhibitory effect on LPS induced IL1$\beta$ and IL12. In some embodiments, the compounds inhibit PDE4 production. In other embodiments, the compounds inhibit both TNF-$\alpha$ production and PDE4 production.

In some embodiments, provided herein are methods of treating, preventing and/or managing a disease selected from dermatological diseases, rheumatic diseases and inflammatory diseases in human including, but not limited to, men, women, and children. In certain embodiments, the disease is dermatomyositis, prurigo nodularis, pyoderma gangrenosum, alopecia areata, hidradenitis suppurtiva, rosacea, lichen planus, giant cell arteritis, Sjogren's syndrome, gout, chronic prostatitis, posterior uveitis, vulvodynia or interstitial cystitis. In some embodiments, the dermatological diseases include dermatomyositis, prurigo nodularis, pyoderma gangrenosum, alopecia areata, hidradenitis suppurtiva, rosacea and lichen planus. In certain embodiments, the rheumatic diseases include giant cell arteritis, Sjogren's syndrome and gout. In some embodiments, the inflammatory diseases include chronic prostatitis, posterior uveitis, vulvodynia and interstitial cystitis.

In another aspect, provided herein are methods of treating, preventing and/or managing a disease selected from dermatomyositis, prurigo nodularis, pyoderma gangrenosum, alopecia areata, hidradenitis suppurtiva, rosacea, lichen planus, giant cell arteritis, Sjogren's syndrome, gout, chronic prostatitis, posterior uveitis, vulvodynia and interstitial cystitis with a therapeutically or prophylactically effective amount of (+)-2-[1-(3-ethoxy-4-methoxyphenyl)-2-methylsulfonyl-ethyl]-4-acetylaminoisoindoline-1,3-dione, or a pharmaceutically acceptable salt or solvate (e.g., hydrate) thereof. In some embodiments, the compound is free of its (−)-enantiomer. In certain embodiments, a salt or solvate of the compound is used. In other embodiments, the free compound is used.

In another aspect, provided herein are methods of treating, preventing and/or managing a disease selected from dermatomyositis, prurigo nodularis, pyoderma gangrenosum, alopecia areata, hidradenitis suppurtiva, rosacea, lichen planus, giant cell arteritis, Sjogren's syndrome, gout, chronic prostatitis, posterior uveitis, vulvodynia and interstitial cystitis with a therapeutically or prophylactically effective amount of cyclopropyl{2-[(1S)-1-(3-ethoxy-4-methoxyphenyl)-2-(methylsulfonyl)ethyl]-3-oxoisoindolin-4-yl}carboxamide, or a pharmaceutically acceptable salt or solvate (e.g., hydrate) thereof. In some embodiments, the compound is free of its (R)-enantiomer. In certain embodiments, a salt or solvate of the compound is used. In other embodiments, the free compound is used.

In some embodiments, the methods further comprise administrating a therapeutically effective amount of at least a second active agent which may be an anti-inflammatory such as non-steroidal agents (e.g., salicylates) or corticosteroids (e.g., dexamethasone), an anti-malarial, an immunosuppressant, an antibiotic, an antiviral, an immunologic-enhancing drug, a hormone, PGE2 or a combination thereof.

In another embodiment, the compound of the invention or a pharmaceutically acceptable salt, solvate or stereoisomer thereof is administered topically in a dosage form which includes, but is not limited to, ointments, creams, gels, pastes, dusting powders, lotions, sprays, liniments, poultices, aerosols, solutions, emulsions, suspensions and combinations thereof.

In further embodiments, the compound of the invention or a pharmaceutically acceptable salt, solvate or stereoisomer thereof is administered parenterally or orally or in a controlled-release manner.

5. BRIEF DESCRIPTION OF THE FIGURES

6. DETAILED DESCRIPTION

Figure 1:
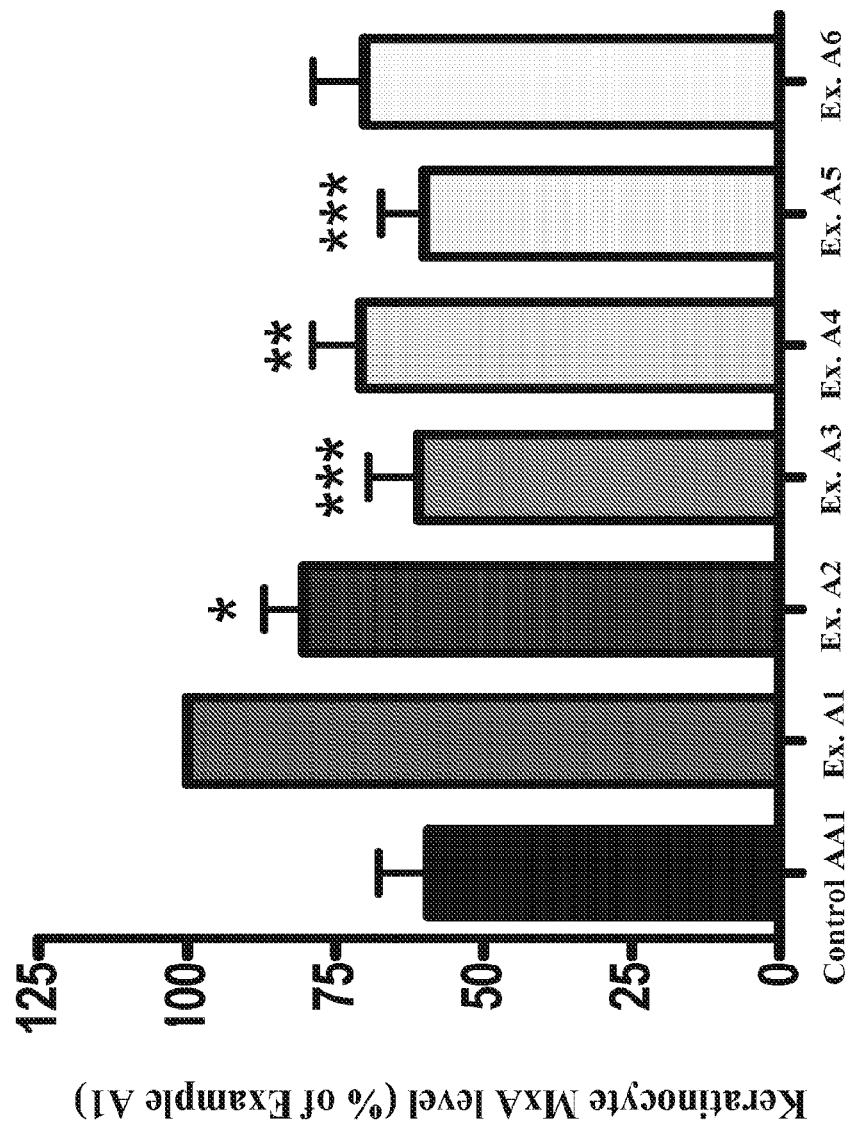
FIG. 1 illustrates the keratinocyte MxA levels of different samples including Control AA1 and Examples A1-A6 used in Example 14.

In one aspect, provided herein are methods of treating, managing and/or preventing a disease selected from dermatomyositis, prurigo nodularis, pyoderma gangrenosum, alopecia areata, hidradenitis suppurtiva, rosacea, lichen planus, giant cell arteritis, Sjogren's syndrome, gout, chronic prostatitis, posterior uveitis, vulvodynia, interstitial cystitis and combinations thereof, wherein the methods comprise administering to a patient having the disease a therapeutically or prophylactically effective amount of (+)-2-[1-(3-ethoxy-4-methoxyphenyl)-2-methylsulfonylethyl]-4-acetylaminoisoindoline-1,3-dione, or a pharmaceutically acceptable salt or solvate thereof. In some embodiments, the compound is substantially free of its (−)-enantiomer.

In another aspect, provided herein are methods of treating, managing and/or preventing a disease selected from dermatomyositis, prurigo nodularis, pyoderma gangrenosum, alopecia areata, hidradenitis suppurtiva, rosacea, lichen planus, giant cell arteritis, Sjogren's syndrome, gout, chronic prostatitis, posterior uveitis, vulvodynia, interstitial cystitis and combinations thereof, wherein the methods comprise administering to a patient having the disease a therapeutically or prophylactically effective amount of cyclopropyl{2-[(1S)-1-(3-ethoxy-4-methoxyphenyl)-2-(methylsulfonyl)ethyl]-3-oxoisoindolin-4-yl}carboxamide, or a pharmaceutically acceptable salt or solvate thereof. In some embodiments, the compound is substantially free of its (R)-enantiomer.

Furthermore, the patients to be treated may include mammals, particularly human. Children and adults can be treated by the methods and compositions disclosed herein. Immunocompromised patients may also be treated. This invention contemplates treatment of patients that have not used other therapies, those that have used other therapies and those that are refractory to therapies for the diseases disclosed herein. In some embodiments, the patient is a female. In certain embodiments, the patient is a male. In other embodiments, the patient is a child.

In some embodiments, the disease to be treated, prevented and/or managed is dermatomyositis. In general, dermatomyositis is characterized by inflammatory and degenerative changes in the skin and muscles. Dermatomyositis may affect both children and adults with overall females/male ratio of about 2:1. Symptoms of dermatomyositis generally include muscle weakness, joint manifestations, visceral involvement and skin changes.

Five diagnostic criteria may be used for the diagnosis of dermatomyositis, which are (i) symmetrical proximal muscle weakness of the limb girdle muscles and anterior neck flexors, with or without dysphagia or respiratory muscle involvement; (ii) elevation of serum levels of skeletal-muscle enzymes; (iii) evidence of an inflammatory myopathy on muscle biopsy; (iv) electromyographic features of a myopathy; and (v) characteristic cutaneous eruption. The presence of three or four criteria plus the cutaneous rash in a patient may define a definitive diagnosis for dermatomyositis.

Dermatomyositis can be classified in different ways. One way is to divide it into adult-onset and juvenile-onset. Each group can be further divided into subgroups. The subgroups of adult-onset include classic dermatomyositis, classic dermatomyositis with malignancy, classic dermatomyositis of an overlap connective tissue disorder and amyopathic dermatomyositis. The subgroups of juvenile-onset include classic dermatomyositis, amyopathic dermatomyositis and hypomyopathic dermatomyositis.

Another possible way to classify dermatomyositis is to divide it into classic dermatomyositis, juvenile dermatomyositis, classic dermatomyositis with malignancy, classic dermatomyositis of an overlap connective tissue disorder, amyopathic dermatomyositis, hypomyopathic dermatomyositis, drug-induced dermatomyositis and post-myopathic dermatomyositis.

The cause of dermatomyositis is uncertain. However, some factors, such as (i) environmental factors; (ii) genetic factors; (iii) certain infectious agents; and (iv) certain drugs, have been implicated. One environmental factor that has been suggested as a causative factor in dermatomyositis is ultraviolet (UV) light. Genetic predisposition linked to certain human leukocyte antigen (HLA) types may be one of the factors of developing dermatomyositis.

Certain infectious agents may be possible triggers of dermatomyositis. Some non-limiting examples include viruses, such as coxsackie virus, parvovirus, echovirus, human T-cell lymphotropic virus (HTLV-1) and human immunodeficiency virus (HIV), bacteria, such as *borrelia burgdorferi* and group A alpha-hemolytic streptococci, and parasites, such as *toxoplasma gondii*.

Certain drugs such as the cholesterol-lowering drugs, some non-steroidal anti-inflammatory drugs (NSAIDs), antineoplastic drugs, anti-infectious drugs and other unrelated medicines are suspected in the pathogenesis of dermatomyositis.

Dermatomyositis can be treated by the compounds of the invention (e.g., (+)-2-[1-(3-ethoxy-4-methoxyphenyl)-2-methylsulfonylethyl]-4-acetylaminoisoindoline-1,3-dione and cyclopropyl{2-[(1S)-1-(3-ethoxy-4-methoxyphenyl)-2-(methylsulfonyl)ethyl]-3-oxoisoindolin-4-yl}carboxamide) in combination with immunosuppressive medication, such as corticosteroids (e.g., prednisone), immunosuppressive agents (e.g., methotrexate, azathioprine, mycophenolate, sirolimus, rituximab, cyclosporine A, cyclophamide, micophenolate mofetil, chlorambucil, fludarabine and aminoquinolone antimalarials), intravenous immunoglobulins (IVIG) and antimalarial drugs (e.g., hydroxychloroquine and chloroquine phosphate).

In some embodiments, the disease to be treated, prevented and/or managed is prurigo nodularis (PN). PN is also known as Hyde prurigo nodularis, Picker nodules, lichen simplex chronicus or lichen corneus obtusus. PN is a dermatologic condition characterized by the presence of papules and nodules with primary intense pruritus. Both sexes may be equally affected. Nearly 80% of patients having PN have a personal or family history of atopic dermatitis, asthma or hay fever compared with approximately 25% of the normal population.

The cause of PN is uncertain. Reaction to an insect bite or another dermatitis may lead to PN. PN may also be associated with emotional stress, iron deficiency anaemia, HIV, chronic renal failure, gluten enteropathy, mycobacterial infection, thyroid diseases, autoimmune diseases and other conditions.

PN nodules or papules are generally 3-20 mm in diameter. They are generally discrete, scaly, symmetric, hyperpigmented or purpuric and firm. Nodules and papules may occur on the extensor surfaces of the arms, the legs and the trunk.

PN lesions may show signs of excoriation with flat, umbilicated or crusted top. Lesions may number from 1-2 to hundreds. Itching is one of the clinical features of PN. The itching is intense and can last for many hours without relief and may disturb sleep.

In certain embodiments, the disease to be treated, prevented and/or managed is pyoderma gangrenosum (PG). PG is a noninfectious neutrophilic dermatosis. It can occur at any age with a possible slight female predominance. About fifty percent of PG cases are associated with an underlying systemic disease.

PG generally starts with sterile pustules that rapidly progress and turn into painful ulcers of variable depth and size with undermined violaceous borders. The legs may commonly be affected but other parts of the skin and mucous membranes may also be involved.

The cause of PG is uncertain. It may be associated with vasclitis, gammopathies, rheumatoid arthritis (RA), leukemia, lymphoma, hepatitis C, systemic lupus erythematosus (SLE), polyarthritis and inflammatory bowel disease. It may be caused by an abnormal immune response.

Diagnosis of PG can be difficult. Biopsy specimen may not provide any pathognomonic information. Diagnosis of PG may be by excluding other causes of cutaneous ulcers through biopsy, culture and clinical acumen.

PG can be generally classified into eight types including classic PG, atypical PG, pustular PG, vegetative PG, peristomal PG, genital PG, PG in infants and children, and extracutaneous neutrophilic disease.

In some embodiments, the disease to be treated, prevented and/or managed is alopecia areata (AA). AA is a disease in which hair is lost in people with no obvious skin disorder or systemic disease.

AA is an autoimmune disease affecting genetically susceptible people exposed to unclear environmental triggers, such as infection and emotional stress. It may coexist with autoimmune vitiligo or thyroiditis.

Diagnosis of AA may be by inspection. AA commonly manifests as a sudden loss of hair in well-demarcated, localized areas. The lesion may be a round or oval patch of alopecia and may be isolated or numerous. The patch of alopecia usually has a distinctive border where normal hair demarcates the periphery of the lesion. The scalp and beard may be frequently affected, but any hairy areas may be involved.

AA can be classified based on the extent or pattern of the hair loss. The hair loss can be present as single delimited patches of hair loss, multiple patches or extensive hair loss. Based on the extent of hair loss, AA is generally classified into patchy AA in which there is a partial loss of scalp hair; alopecia totalis in which there is a 100% loss of scalp hair; and alopecia universalis in which there is a 100% loss of all scalp and body hair.

In certain embodiments, the disease to be treated, prevented and/or managed is hidradenitis suppurativa (HS). HS is also known as Verneuil's disease, pyoderma fistulans significa or acne inversa. HS is a chronic disease characterized by scarring inflammation of apocrine glands of the axillae, groin and around nipples and anus. The incidence of HS may be greater in females than in males. HS may occur after puberty with average age onset in the second or third decades of life. Diagnosis of HS may be by examination.

The cause of HS may be the blockage of apocrine ducts which leads to subsequent inflammation, bacterial overgrowth and scarring. *Staphylococcus aureus* is commonly implicated in acute cases of HS, but gram-negative organisms, such as *Proteus*, may predominate in chronic cases of HS.

Swollen, tender masses resembling cutaneous abscesses may develop in patients having HS. Characteristics in chronic cases of HS include pain, fluctuance, discharge and sinus tract formation. In chronic axillary cases of HS, coalescence of inflamed nodules may cause palpable cordlike fibrotic bands. The condition may become disabling because of pain and foul odor.

In some embodiments, the disease to be treated, prevented and/or managed is rosacea. Rosacea, also known as acne rosacea, is a chronic inflammatory disorder characterized by facial flushing, telangiectasias, erythema, papules, pustules and rhinophyma. Diagnosis may be based on the characteristic appearance and history.

Rosacea commonly affects patients aged about 30 to 50 with fair complexions, notably those of Irish and Northern European descent, but it may affect and probably be under-recognized in darker skinned patients.

The cause of rosacea is uncertain. Abnormal vasomotor control, impaired facial venous drainage, an increase in follicle mites and Helicobacter *pylori* infection may be associated with rosacea. Levels of small antimicrobial peptides, which are part of the body's natural defense system, may be elevated in patients with rosacea. People with rosacea may also have higher than normal levels of cathelicidin as well as stratum corneum tryptic enzymes.

Rosacea is limited to the face and scalp, and manifests in 4 phases including pre-rosacea phase, vascular phase, inflammatory phase and late stage. There are four identified rosacea subtypes, including erythematotelangiectatic rosacea, papulopustular rosacea, phymatous rosacea, ocular rosacea and other variants of rosacea including rosacea conglobata, rosacea fulminans and phymas in rosacea.

In certain embodiments, the disease to be treated, prevented and/or managed is lichen planus (LP). LP is an inflammatory dermatosis. It is a recurrent, pruritic, inflammatory eruption characterized by small, discrete, polygonal, flat-topped, and violaceous papules that may coalesce into rough scaly patches and may accompany oral lesions. Diagnosis of LP may be clinical and supported by skin biopsy. Children may be less frequently affected.

The cause of LP is not entirely understood. LP may be caused by a T cell—mediated autoimmune reaction against basal epithelial keratinocytes in people with genetic predisposition. Drugs, including β-blockers, NSAIDs, ACE inhibitors, sulfonylureas, gold, antimalarial agents and thiazides, may cause LP. It may be associated with hepatitis C—induced liver insufficiency, primary biliary cirrhosis, and other forms of hepatitis.

Typical lesions associated with LP include pruritic, purple, polyangular, flat-topped papules and plaques. Lesions may be 2 to 4 mm in diameter, with angular borders, a violaceous color and a distinct sheen in cross-lighting. They are generally symmetrically distributed and on the flexor surfaces of the legs, wrists, glans penis, trunk and oral and vaginal mucosae, but they can be widespread.

Cutaneous LP may be described by lesion configuration or morphology. Some non-limiting examples of cutaneous LP include blaschkoid LP, zosteriform LP, inverse LP, mucosal LP, lichen planopilaris, hypertrophic LP, bullous LP, actinic LP, annular atrophic LP, erosive LP, LP pigmentosus, perforating LP, invisible LP, LP pemphigoides and LP erythematosus.

In some embodiments, the disease to be treated, prevented and/or managed is giant cell arteritis (GCA). GCA, also known as temporal arteritis, granulomatous arteritis, cranial arteritis or Horton's disease, is a systemic inflammatory vasculitis.

Vasculitis tends to affect arteries containing elastic tissue. Vasculitis may commonly affect the temporal, cranial or other carotid system arteries. The aortic arch branches, coronary arteries and peripheral arteries can also be affected. Mononuclear cells infiltrated in the adventitia form granulomas containing activated T cells and macrophages. Multinucleated giant cells may cluster near the disrupted elastic lamina. The intimal layer may be thickened, with concentric narrowing and occlusion of the lumen.

GCA may involve the thoracic aorta, large arteries emerging from the aorta in the neck and extracranial branches of the carotid arteries. The intracranial vessels are generally not affected.

Symptoms of GCA may begin gradually over several weeks or occur abruptly. Focal symptoms and signs may include headaches, visual disturbances, temporal artery tenderness and pain in the jaw muscles during chewing. Fever, weight loss, malaise and fatigue are also common symptoms. Erythrocyte sedimentation rate (ESR) and level of C-reactive protein of patient with GCA may be elevated. Diagnosis of GCA may be clinical and confirmed by temporal artery biopsy.

GCA is a relatively common form of vasculitis in the US and Europe. Women may be affected more often than men. Mean onset age of GCA is about 70, with a range of about 50 to >90. About 40 to 60% of patients with GCA have polymyalgia rheumatica.

In certain embodiments, the disease to be treated, prevented and/or managed is Sjogren's syndrome (SS). SS is a relatively common chronic, autoimmune, systemic and inflammatory disorder. Characteristics of SS include dryness of the eyes, mouth and other mucous membranes. Dryness may be due to lymphocytic infiltration of the exocrine gland and secondary gland dysfunction. SS can affect various exocrine glands or other organs. Diagnosis of SS may be by specific criteria related to eye, mouth and salivary gland involvement, autoantibodies and histopathology.

All ages can be affected with SS. SS generally occurs among middle-aged women. Patients can be classified as having either primary or secondary SS. Primary SS does not occur in association with other systemic autoimmune disease. However, secondary SS occurs in association with another autoimmune disease, such as RA, SLE, systemic sclerosis, mixed connective tissue disease, primary biliary cirrhosis, Hashimoto's thyroiditis or chronic autoimmune hepatitis.

The cause of SS is uncertain. Salivary, lacrimal and other exocrine glands may become infiltrated with CD4+ T cells and with some B cells. The T cells may produce inflammatory cytokines Salivary duct cells may also produce cytokines, eventually damaging the secretory ducts. Atrophy of secretory epithelium of the lacrimal glands may cause desiccation of the cornea and conjunctiva. Lymphocytic infiltration and intraductal cellular proliferation in the parotid gland may cause luminal narrowing and formation of compact cellular structures termed myoepithelial islands. Atrophy of the gland may result in patient having SS. Dryness, gastrointestinal mucosal or submucosal atrophy, and diffuse infiltration by plasma cells and lymphocytes may cause symptoms of SS. SS may also be associated with genetic predisposition.

In some embodiments, the disease to be treated, prevented and/or managed is gout. Gout is a common arthritis caused by precipitation of momosodium urate crystals into tissue, generally within and around joints. It generally causes recurrent acute or chronic arthritis. Acute arthritis is initially monarticular and generally involves the first metatarsophalangeal joint. Diagnosis of Gout may require identification of crystals in synovial fluid.

Gout may be more common among men than women. In men, gout generally develops during middle age. In women, gout generally develops after menopause. Younger people with gout are less common, but gout is generally more severe in people who develop grout before the age of 30. Gout generally runs in families.

Symptoms of gout include acute pain, tenderness, warmth, redness, swelling and inflammation. Acute gouty arthritis generally begins with sudden onset of pain. The metatarsophalangeal joint of a great toe is commonly involved in the case of gout. The pain may become progressively more severe, generally over a few hours and excruciating. The overlying skin may become warm, tense, shiny and red or purplish. Fever, chills, tachycardia and malaise may occur in patient with gout. Coexisting hypertension, hyperlipidemia and obesity are common in patient with gout.

The greater the degree and duration of hyperuricemia, the greater is the likelihood of gout and the more severe are the symptoms. Urate levels can be elevated because of decreased renal excretion urate, increased production of urate and increased intake of purine-rich foods. However, the association between elevated serum uric acid levels and gout development is uncertain.

In certain embodiments, the disease to be treated, prevented and/or managed is prostatitis. Prostatitis refers to a disparate group of disorders that manifests with a combination of predominantly irritative or obstructive urinary symptoms and perineal pain.

Prostatitis can be classified into 4 categories including acute bacterial prostatitis, chronic bacterial prostatitis, chronic prostatitis/chronic pelvic pain syndrome and asymptomatic inflammatory prostatitis. Chronic bacterial prostatitis and chronic prostatitis/chronic pelvic pain syndrome are generally more common than acute bacterial prostatitis and asymptomatic inflammatory prostatitis.

The cause of chronic prostatitis/chronic pelvic pain syndrome is uncertain. It may be associated with etiological and physiopathological factors. (e.g., immunological, endocrine, neurological, pysychological and infective factors).

Symptoms of chronic prostatitis/chronic pelvic pain syndrome include pain, pain with ejaculation, voiding dysfunction (e.g., urinary irritation and urinary obstruction) and sexual dysfunction. The prostate may be tender but generally may not be boggy or swollen. The discomfort can be significant and may interfere with quality of life.

In certain embodiments, the disease to be treated, prevented and/or managed is uveitis. Uveitis is an eye disorder in which uveal tract, i.e., iris, ciliary body or choroid, is inflamed. Uveitis can be classified into anterior uveitis, intermediate uveitis, posterior uveitis and panuveitis.

In some embodiments, the disease to be treated, prevented and/or managed is posterior uveitis (PU). PU refers to any forms of retinitis, choroiditis or inflammation of the optic disk. PU is generally idiopathic. PU can be diagnosed by dilating the pupil of patient. Toxoplasmosis is a commonly recognized cause of PU in immunocompetent patients. Cytomegalovirus is a commonly recognized cause of PU in patients with human immunodeficiency virus/acquired immunodeficiency syndrome (HIV/AIDS).

PU commonly causes floaters and decreased vision, but symptoms of PU can be diverse. Signs of PU include cells in the vitreous humor; white or yellow-white lesions in the retina and underlying choroid; exudative retinal detachments; retinal vasculitis; and optic disk edema.

In certain embodiments, the disease to be treated, prevented and/or managed is vulvodynia. Vulvodynia is a chronic painful disorder which can be characterized by burning, stinging, irritation or sharp pain in the vulva, including the labia and entrance to the vagina but without the presence of relevant visible findings or a specific, clinically identifiable and neurological disorder.

Symptoms of vulvodynia include burning, stinging, irritation or sharp pain in the vulva. Symptoms may occur in one place or the entire vulvar area. Pain may be constant or intermittent, or happen only when the vulva is touched. It can occur during or after sexual activity, when tampons are inserted, or when prolonged pressure is applied to the vulva or without any particular reason.

Vulvodynia may affect women of all ages. It may interfere with patient's emotion and may lead to depression. Vulvodynia can be classified by the anatomical site of the pain of patient (e.g., generalized vulvodynia, hemivulvodynia and clitorodynia). Vulvodynia can further be classified into provoked, unprovoked and mixed form, i.e., both provoked and unprovoked.

The cause of vulvodynia is uncertain. It may be associated with genetic predisposition to inflammation, allergy or other sensitivity, autoimmune disorder similar to lupus erythematosus, eczema or to lichen sclerosus, infection, injury and neuropathy. It may also be negative outcomes of genital surgery, such as a labiectomy.

In some embodiments, the disease to be treated, prevented and/or managed is interstitial cystitis (IC). IC is noninfectious bladder inflammation. About 90% of cases of IC occur in women. Diagnosis of IC may be by history and exclusion of other disorders clinically and by cystoscopy and biopsy.

The cause of IC is uncertain. It may involve loss of protective urothelial mucin, penetration of urinary potassium and other substances into the bladder wall, activation of sensory nerves or damage of smooth muscle. Mast cells may mediate the process of IC, but their role is unclear.

Symptoms of IC include suprapubic, pelvic and abdominal pain, urinary frequency and urgency with incontinence. IC may worsen as the bladder fills and diminishes when patient voids. Ovulation, menstruation, seasonal allergies, physical stress, emotional stress or sexual intercourse may worsen the symptoms of IC. The symptoms may appear and worsen over years as the bladder wall of patient is damaged. Foods with high potassium content may cause exacerbations of IC. Alcohol, tobacco and spicy foods may worsen the symptoms of IC.

6.1 Definitions

As used herein and unless otherwise indicated, the term "the compound of the invention" includes, but is not limited to, (+)-2-[1-(3-ethoxy-4-methoxyphenyl)-2-methylsulfonylethyl]-4-acetylaminoisoindoline-1,3-dione, cyclopropyl{2-[(1S)-1-(3-ethoxy-4-methoxyphenyl)-2-(methylsulfonyl)ethyl]-3-oxoisoindolin-4-yl}carboxamide, pharmaceutically acceptable prodrugs, metabolites, polymorphs, salts, solvates, stereoisomers and clathrates thereof, and combinations thereof.

As used herein and unless otherwise indicated, the term "pharmaceutically acceptable salt" includes, but is not limited to, salts of acidic or basic groups that can be present in the compounds of the invention. Under certain acidic conditions, the compound of the invention can form a wide variety of salts with various inorganic and organic acids. The acids that can be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide and pamoate. Under certain basic conditions, the compound of the invention can form base salts with various pharmacologically acceptable cations. Non-limiting examples of such salts include alkali metal or alkaline earth metal salts and, particularly, calcium, magnesium, sodium, lithium, zinc, potassium and iron salts.

As used herein and unless otherwise indicated, the term "hydrate" means a compound of the present invention or a salt thereof, that further includes a stoichiometric or non-stoichiometric amount of water bound by non-covalent intermolecular forces.

As used herein and unless otherwise indicated, the term "solvate" means a solvate formed from the association of one or more solvent molecules to a compound of the present invention. The term "solvate" includes hydrates (e.g., monohydrate, dihydrate, trihydrate, tetrahydrate and the like).

As used herein and unless otherwise indicated, the term "polymorph" means solid crystalline forms of a compound of the present invention or complex thereof. Different polymorphs of the same compound can exhibit different physical, chemical and/or spectroscopic properties.

As used herein and unless otherwise specified, the term "prodrug" means a derivative of a compound that can hydrolyze, oxidize, or otherwise react under biological conditions (in vitro or in vivo) to provide the compound. Examples of prodrugs include, but are not limited to, derivatives and metabolites of (+)-2-[1-(3-ethoxy-4-methoxyphenyl)-2-methylsulfonylethyl]-4-acetylaminoisoindoline-1,3-dione, or cyclopropyl{2-[(1S)-1-(3-ethoxy-4-methoxyphenyl)-2-(methylsulfonyl)ethyl]-3-oxoisoindolin-4-yl}carboxamide that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described by 1 *Burger's Medicinal Chemistry and Drug Discovery*, 172-178, 949-982 (Manfred E. Wolff ed., 5th ed. 1995).

As used herein, and unless otherwise specified, the terms "biohydrolyzable carbamate," "biohydrolyzable carbonate," "biohydrolyzable ureide" and "biohydrolyzable phosphate" mean a carbamate, carbonate, ureide and phosphate, respectively, of a compound that either: 1) does not interfere with the biological activity of the compound but can confer upon that compound advantageous properties in vivo, such as uptake, duration of action or onset of action; or 2) is biologically inactive but is converted in vivo to the biologically active compound. Non-limiting examples of biohydrolyzable carbamates include lower alkylamines, substituted ethylenediamines, aminoacids, hydroxyalkylamines, heterocyclic and heteroaromatic amines and polyether amines.

As used herein, and unless otherwise specified, the term "stereoisomer" encompasses all enantiomerically/stereomerically pure and enantiomerically/stereomerically enriched compounds of this invention.

As used herein, and unless otherwise indicated, the term "stereomerically pure" or "enantiomerically pure" means that a compound comprises one stereoisomer and is substantially free of its counter stereoisomer or enantiomer. For example, a compound is stereomerically or enantiomerically pure when the compound contains 80%, 90% or 95% or more of one stereoisomer and 20%, 10% or 5% or less of the counter stereoisomer. In some cases, a compound of the invention is considered optically active or stereomerically/enantiomerically pure (e.g., substantially the R-form or substantially the S-form) with respect to a chiral center when the compound is about 80% ee (enantiomeric excess) or greater, preferably, equal to or greater than 90% ee with respect to a particular chiral center and more preferably 95% ee with respect to a particular chiral center.

As used herein, and unless otherwise indicated, the term "substantially free of its (R)-enantiomer" is used herein to mean equal to or greater than 80% pure of the (S)-enantiomer, based upon the total weight of the compound. In some instances, the term "substantially free of its (R)-enantiomer" means equal to or greater than 85%, 90%, 95% or 99% pure of the (S)-enantiomer, based upon the total weight of the compound.

As used herein, and unless otherwise indicated, the term "substantially free of its (−) enantiomer" is used herein to mean equal to or greater than 80% pure of the (+) enantiomer, based upon the total weight of the compound. In some instances, the term "substantially free of its (−) enantiomer" means equal to or greater than 85%, 90%, 95% or 99% pure of the (+) enantiomer, based upon the total weight of the compound.

As used herein, and unless otherwise indicated, the term "stereomerically enriched" or "enantiomerically enriched" encompasses certain mixtures of stereoisomers of compounds of this invention (e.g., R/S=30/70, 35/65, 65/35 and 70/30).

As used herein, and unless otherwise specified, the terms "treat," "treating" and "treatment" contemplate an action that occurs while a patient is suffering from the specified disease or disorder, which reduces the severity or symptoms of the disease or disorder, or retards or slows the progression or symptoms of the disease or disorder.

As used herein, and unless otherwise specified, the term "therapeutically effective amount" encompasses dosage amounts and dose frequency schedules. Different therapeutically effective amounts may be applicable for different conditions, as will be readily known by those of ordinary skill in the art. Similarly, amounts sufficient to treat or prevent specific disorders, but insufficient to cause, or sufficient to reduce, adverse effects associated with the compounds of the invention are also encompassed by dosage amounts and dose frequency schedules.

As used herein, and unless otherwise specified, the terms "prevent," "preventing" and "prevention" contemplate an action that occurs before a patient begins to suffer from the specified disease or disorder, which inhibits or reduces the severity or symptoms of the disease or disorder.

As used herein, and unless otherwise indicated, the terms "manage," "managing" and "management" encompass preventing the recurrence of the specified disease or disorder in a patient who has already suffered from the disease or disorder and/or lengthening the time that a patient who has suffered from the disease or disorder remains in remission. The terms encompass modulating the threshold, development and/or duration of the disease or disorder, or changing the way that a patient responds to the disease or disorder.

As used herein, and unless otherwise specified, the term "enhancing" or "enhance," when used in connection with immune response, means that when an antigenic or immunogenic agent is administered to a subject who has been or is being treated with the compounds of the invention, there is an increased antibody formation, as compared to a subject to which same amount of the antigenic or immunogenic agent alone is administered, as determined by any conventional methods of antibody level determination known in the art, for example, nephelometry, immunoelectrophoresis, radioimmunoassay and ELISA. In some embodiments, when methods of this invention are used, antibody formation is increased by about 5%, 10%, 20%, 50% or 100% or more, as compared to the antibody formation obtained when such methods are not used.

6.2 The Compounds Of The Invention

(+)-2-[1-(3-Ethoxy-4-Methoxyphenyl)-2-Methyl Sulfonylethyl]-4-Acetylaminoisoindoline-1,3-Dione Provided herein are methods of treating, managing or preventing a disease selected from dermatomyositis, prurigo nodularis, pyoderma gangrenosum, alopecia areata, hidradenitis suppurtiva, rosacea, lichen planus, giant cell arteritis, Sjogren's syndrome, gout, chronic prostatitis, posterior uveitis, vulvodynia, interstitial cystitis and combinations thereof, wherein the methods comprises administering to a patient in need of such treatment, management or prevention a therapeutically or prophylactically effective amount of (+)-enantiomer of (+)-2-[1-(3-ethoxy-4-methoxyphenyl)-2-methylsulfonylethyl]-4-acetylaminoisoindoline-1,3-dione (also known as apremilast).

Without being limited by theory, the (+)-enantiomer of (+)-2-[1-(3-ethoxy-4-methoxyphenyl)-2-methylsulfonylethyl]-4-acetylaminoisoindoline-1,3-dione is believed to be (S)-{2-[1-(3-ethoxy-4-methoxyphenyl)-2-methylsulfonylethyl]-4-acetylaminoisoindoline-1,3-dione} [Compound (I)], which has the following structure:

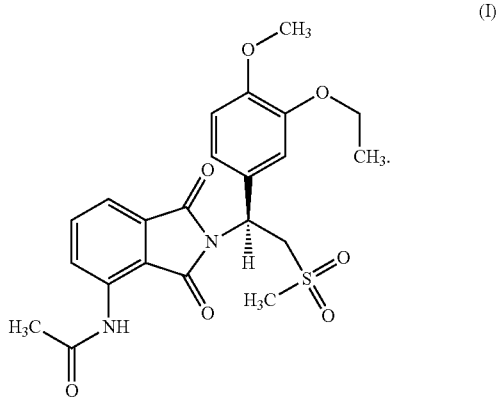

(I)

Thus, (+)-2-[1-(3-ethoxy-4-methoxyphenyl)-2-methylsulfonylethyl]-4-acetylaminoisoindoline-1,3-dione is used to describe the compound depicted as Compound (I). Compound (I) can be prepared according to methods disclosed in U.S. Pat. No. 6,962,940, titled "(+)-2-[1-(3-Ethoxy-4-methoxyphenyl)-2-methylsulfonylethyl]-4-acetylaminoisoindoline-1,3-dione: Methods Of Using And Compositions Thereof," issued Nov. 8, 2005, which is incorporated herein by reference. In one embodiment, Compound (I) is synthesized from 3-acetamidophthalic anhydride and a chiral amino acid salt of (S)-2-(3-ethoxy-4-methoxyphenyl)-1-(methylsulphonyl)-eth-2-ylamine. Chiral amino acid salts of (S)-2-(3 ethoxy-4-methoxyphenyl)-1-(methylsulphonyl)-eth-2-ylamine include, but not limited to salts formed with the L isomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, 4-aminobutyric acid, 2-aminoisobutyric acid, 3-aminopropionic acid, ornithine, norleucine, norvaline, hydroxyproline, sarcosine, citrulline, cysteic acid, t-butylglycine, t-butylalanine, phenylglycine, cyclohexylalanine, and N-acetyl-L-leucine. In some embodiments, the chiral amino acid salt is (S)-2-(3-ethoxy-4-methoxyphenyl)-1-(methylsulphonyl)-eth-2-ylamine-N-acetyl-L-leucine salt, which is resolved from 2-(3-ethoxy-4-methoxyphenyl)-1-(methylsulphonyl)-eth-2-ylamine and N-acetyl-L-leucine in methanol.

Alternatively, Compound (I) can be isolated from the corresponding racemic 2-[1-(3-ethoxy-4-methoxyphenyl)-2-methylsulfonylethyl]-4-acetylaminoisoindoline-1,3-dione by separation techniques known in the art. The racemic compound can be readily prepared according to the procedure for Example 12 of U.S. Pat. No. 6,020,358, which is incorporated herein by reference. Examples of suitable separation techniques include, but are not limited to, the formation of chiral salts and the use of chiral or high performance liquid chromatography "HPLC" and the formation and crystallization of chiral salts. See, e.g., Jacques, J., et al., *Enantiomers, Racemates and Resolutions* (Wiley Interscience, New York, 1981); Wilen, S. H., et al., Tetrahedron 33:2725 (1977); Eliel, E. L., *Stereochemistry of Carbon Compounds* (McGraw Hill, N.Y., 1962); and Wilen, S. H., *Tables of Resolving Agents and Optical Resolutions* p. 268 (E. L. Eliel, Ed., Univ. of Notre Dame Press, Notre Dame, Ind., 1972), all of which are incorporated herein by reference in their entirety.

Cyclopropyl{2-[(1S)-1-(3-Ethoxy-4-Methoxyphenyl)-2-(Methylsulfonyl)Ethyl]-3-Oxoisoindolin-4-yl}Carboxamide Provided herein are methods of treating, managing or preventing a disease selected from dermatomyositis, prurigo nodularis, pyoderma gangrenosum, alopecia areata, hidradenitis suppurtiva, rosacea, lichen planus, giant cell arteritis, Sjogren's syndrome, gout, chronic prostatitis, posterior uveitis, vulvodynia, interstitial cystitis and combinations thereof, wherein the methods comprise administering to a patient in need of such treatment, management or prevention a therapeutically or prophylactically effective amount of cyclopropyl{2-[(1S)-1-(3-ethoxy-4-methoxyphenyl)-2-(methylsulfonyl)ethyl]-3-oxoisoindolin-4-yl}carboxamide or N-[2-[(1S)-1-(3-ethoxy-4-methoxyphenyl)-2-(methylsulfonyl)ethyl]-2,3-dihydro-3-oxo-1H-isoindol-4-yl]-cyclopropanecarboxamide.

Cyclopropyl{2-[(1S)-1-(3-ethoxy-4-methoxyphenyl)-2-(methylsulfonyl)ethyl]-3-oxoisoindolin-4-yl}carboxamide or N-[2-[(1S)-1-(3-ethoxy-4-methoxyphenyl)-2-(methylsulfonyl)ethyl]-2,3-dihydro-3-oxo-1H-isoindol-4-yl]-cyclopropanecarboxamide [i.e., Compound (II)] has the following structure:

Compound (II)

Compound (II) can be prepared according to the preparation procedure for Example 57 of U.S. Pat. No. 6,667,316, titled "Pharmaceutically Active Isoindoline Derivatives," issued Dec. 23, 2003, which is incorporated herein by reference in its entirety. In one embodiment, Compound (II) can be prepared by heating a mixture of 7-amino-2-[(1S)-1-(3-ethoxy-4-methoxyphenyl)-2-(methylsulfonyl)ethyl]isoindolin-1-one and cyclopropanecarbonyl chloride in tetrahydrofuran.

Alternatively, Compound (II) can be isolated from the corresponding racemic cyclopropyl{2-[1-(3-ethoxy-4-methoxyphenyl)-2-(methylsulfonyl)ethyl]-3-oxoisoindolin-4-yl}carboxamide by separation techniques known to skilled artisans. The racemic compound can be readily prepared according to the preparation procedure for Example 55 of U.S. Pat. No. 6,667,316. Examples of suitable separation techniques include, but are not limited to, the formation of chiral salts and the use of chiral or high performance liquid chromatography "HPLC" and the formation and crystallization of chiral salts. See, e.g., Rex W. Souter, *Chromatographic Separations of Stereoisomers*, (CRC Press, Boca Raton, 1985); Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, N.Y., 1962); and Wilen, S. H., *Tables of Resolving Agents and Optical Resolutions*, p. 268 (E. L. Eliel, Ed., Univ. of Notre Dame Press, Notre Dame, Ind., 1972), all of which are incorporated herein by reference in their entirety.

6.3 Methods Of Treatments And Prevention

Provided herein are methods for treating, preventing and/or managing a disease selected from dermatomyositis, prurigo nodularis, pyoderma gangrenosum, alopecia areata, hidradenitis suppurtiva, rosacea, lichen planus, giant cell arteritis, Sjogren's syndrome, gout, chronic prostatitis, posterior uveitis, vulvodynia and interstitial cystitis by administering one or more of the compounds of the invention to a patient having the disease.

In some embodiments, the disease is dermatomyositis (DM). Some non-limiting examples of DM include classic dermatomyositis, juvenile dermatomyositis, classic dermatomyositis with malignancy, classic dermatomyositis of an overlap connective tissue disorder, amyopathic dermatomyositis, hypomyopathic dermatomyositis, drug-induced dermatomyositis and post-myopathic dermatomyositis.

In some embodiments, the disease is prurigo nodularis (PN).

In certain embodiments, the disease is pyoderma gangrenosum (PG). Some non-limiting examples of PG include classic PG, atypical PG, pustular PG, vegetative PG, peristomal PG, genital PG, PG in infants and children and extracutaneous neutrophilic disease.

In some embodiments, the disease is alopecia areata (AA). Some non-limiting examples of AA include patchy AA, alopecia totalis and alopecia universalis.

In certain embodiments, the disease is hidradenitis suppurativa (HS).

In some embodiments, the disease is rosacea or acne rosacea. Some non-limiting examples of rosacea or acne rosacea include erythematotelangiectatic rosacea, papulopustular rosacea, phymatous rosacea, ocular rosacea, and other variants of rosacea including such as rosacea conglobata, rosacea fulminans and phymas in rosacea.

In certain embodiments, the disease is lichen planus (LP). Some non-limiting examples of LP include blaschkoid LP, zosteriform LP, inverse LP, mucosal LP, lichen planopilaris, hypertrophic LP, bullous LP, actinic LP, annular atrophic LP, erosive LP, LP pigmentosus, perforating LP, invisible LP, LP pemphigoides and LP erythematosus.

In some embodiments, the disease is giant cell arteritis (GCA), temporal arteritis, granulomatous arteritis, cranial arteritis or Horton's disease.

In certain embodiments, the disease is Sjogren's syndrome (SS).

In some embodiments, the disease is gout.

In certain embodiments, the disease is prostatitis. Some non-limiting examples of prostatitis include acute bacterial prostatitis, chronic bacterial prostatitis, chronic prostatitis/chronic pelvic pain syndrome and asymptomatic inflammatory prostatitis.

In some embodiments, the disease is posterior uveitis (PU).

In certain embodiments, the disease is vulvodynia. Some non-limiting examples of vulvodynia include generalized vulvodynia, hemivulvodynia and clitorodynia.

In some embodiments, the disease is interstitial cystitis (IC).

This invention also encompasses the uses of the compounds of the invention in modulating the immune system to keep it from slipping into imbalance and producing inflammatory, autoimmune and related disorders such as the diseases disclosed herein in a patient. Therefore, in another embodiment, this invention encompasses methods of enhancing an immune response to an immunogen, comprising administering a therapeutically or prophylactically effective amount of (+)-2-[1-(3-ethoxy-4-methoxyphenyl)-2-methylsulfonylethyl]-4-acetylaminoisoindoline-1,3-dione, or cyclopropyl 2-[(1S)-1-(3-ethoxy-4-methoxyphenyl)-2-(methylsulfonyl)ethyl]-3-oxoisoindolin-4-yl}carboxamide, or a pharmaceutically acceptable salt or solvate thereof, to a patient in need of such enhancement. The compounds can be administered prior to, during or subsequent to the patient's exposure to the immunogen.

6.3.1 Combination Therapy With A Second Active Agent

In particular methods encompassed by this embodiment, the compound of the invention is administered in combination with another drug ("second active agent") in methods of treating, managing and/or preventing one or more diseases disclosed herein. The second active agent includes, but is not limited to, anti-inflammatory agents such as non-steroidal agents and corticosteroids, anti-malarials, immunosuppressants, antibiotics, antivirals, immunologic-enhancing drugs, hormones, PGE2 and combinations thereof. Non-limiting examples of methods or therapies that can be used in combination with the administration of the compound of the invention include antibody injections or infusions, and stem cell transplantation.

The compound of the invention can be used with at least a second active agent in methods of the invention disclosed herein. This invention encompasses synergistic combinations for the treatment, prevention and/or management of one or more diseases disclosed herein. The compound of the invention can also be used to alleviate adverse or unnamed effects associated with some second active agents, and conversely some second active agents can be used to alleviate adverse or unnamed effects associated with the compound of the invention.

In some embodiments of interest, the second active agents may include, but are not limited to, anti-inflammatories such as, but not limited to, acetaminophen (e.g., TYLENOL®), 5-aminosalicylic acid derivatives, salicylates, corticosteroids and nonsteroidal anti-inflammatory drugs. A non-limiting example of 5-aminosalicylic acid derivatives is sulfasalazine (e.g., AZULFIDINE®). A non-limiting example of salicylates is acetylsalicylic acid (e.g., ASPIRIN®).

Non-limiting examples of corticosteroids include dexamethasone (e.g., AZIUM® or VOREN®), hydrocortisone (e.g., CETACORT®, HYTONE® or NUTRACORT®), beclomethasone (e.g., VANCERIL®), budesonide (e.g., PULMICORT®), fluticasone (e.g., FLONASE® or FLOVENT®), methylprednisolone (e.g., DEPO-MEDROL®, SOLU-MEDROL® or MEDROL®), mometasone furoate (e.g., NASONE® or ELOCON®), prednisone (e.g., DELTASONE®, ORASON®, PREDNICEN-M® or LIQUID PRED®) and triamcinolone (e.g., AZMACORT®).

Non-limiting examples of nonsteroidal anti-inflammatory drugs include diclofenac (e.g., ARTHROTEC®), diflunisal (e.g., DOLOBID®), etodolac (e.g., LODINE®) fenoprofen (e.g., NALFON®), ibuprofen (e.g., ADVIL®, CHILDREN'S ADVIL/MOTRIN®, MEDIPREN®, MOTRIN®, NUPRIN® or PEDIACARE FEVER®), indomethacin (e.g., ARTHREXIN®), ketoprofen (e.g., ORUVAIL®), ketorolac (e.g., TORADOL®), fosfomycin tromethamine (e.g., MONURAL®), meclofenamate (e.g., Meclomen®), nabumetone (e.g., RELAFEN®), naproxen (e.g., ANAPROX®, ANAPROX® DS, EC-NAPROSYN®, NAPRELAN® or NAPROSYN®), oxaprozin (e.g., DAYPRO®), piroxicam (e.g., FELDENE®), sulindac (e.g., CLINORIL®), and tolmetin (e.g., TOLECTIN® DS or TOLECTIN®).

In other embodiments of interest, the second active agents may include, but are not limited to, anti-malarials such as chloroquine (e.g., ARALEN®) and hydroxychloroquine (e.g., PLAQUENIL®); immunosuppressants such as azathioprine (e.g., IMURAN®), cyclophosphamide (e.g., CYTOXAN®), chlorambucil (e.g., LEUKERAN®) and melphalan (e.g., ALKERAN®); and immunomodulatory compounds such as azathioprine (e.g., IMURAN®), cyclophosphamide (e.g., CYTOXAN®), methotrexate (e.g., RHEUMATREX®) and cyclosporin (e.g., NEORAL® or SANDIMMUNE®).

In further embodiments of interest, the second active agents may include, but are not limited to, antibiotics (therapeutic or prophylactic) such as, but not limited to, ampicillin (e.g., UNASYN®), tetracycline (e.g., ACHROMYCIN® or SUMYCIN®), penicillin (e.g., AMOXIL®, POLYMOX®, TRIMOX®, SPECTROBID® or GEOCILLIN®), cephalosporins (e.g., OMNICEF®, SPECTRACEF®, SUPRAX®, VANTIN®, CEFZIL® or CEDAX®), streptomycin (e.g., ZANOSAR®), kanamycin (e.g., KANTREX®) and erythromycin (e.g., E.E.S.®, E-MYCIN®, ERYC®, ERY-TAB®, ERYTHROCIN® or PCE®); antivirals such as, but not limited to, amantadine (e.g., SYMMETREL®), rimantadine (e.g., FLUMADINE®), acyclovir (e.g., ZOVIRAX®) and ribavirin (e.g., VIRAZOLE®); immunoglobulin; immunologic enhancing drugs such as, but not limited to, levamisole (e.g., ERGAMISOL®) and inosine pranobex (ISOPRINOSINE®); biologics such as, but not limited to, gamma-globulin, transfer factor, interleukins and interferons; hormones such as, but not limited to, thymic; and other immunologic agents such as, but not limited to, B cell stimulators (e.g., BAFF/BlyS), cytokines (e.g., IL-2, IL-4 and IL-5), growth factors (e.g., TGF-β), antibodies (e.g., anti-CD40 and IgM), oligonucleotides containing unmethylated CpG motifs (e.g., TCGTCGTTTTGTCGTTTTGTCGTT) and vaccines (e.g., viral and tumor peptide vaccines).

Specific methods of the invention comprise administering (+)-2-[1-(3-ethoxy-4-methoxyphenyl)-2-methylsulfonylethyl]-4-acetylaminoisoindoline-1,3-dione, or cyclopropyl 2-[(1S)-1-(3-ethoxy-4-methoxyphenyl)-2-(methylsulfonyl)ethyl]-3-oxoisoindolin-4-yl}carboxamide, or a pharmaceutically acceptable salt, or solvate thereof, in combination with at least a second active agent or another therapy.

The amount of second active agent administered can be determined based on the specific agent used, the type of disease being treated or managed, the severity and stage of disease, and the amount(s) of the compounds of the invention and any optional additional second active agents concurrently administered to the patient. Those of ordinary skill in the art can determine the specific amounts according to conventional procedures known in the art. In the beginning, one can start from the amount of the second active agent that is conventionally used in the therapies and adjust the amount according to the factors described above. See, e.g., *Physician's Desk Reference* ($56^{th}$ Ed., 2004). Further, the amounts and methods of administration of the second active agents disclosed herein for the treatment, prevention and/or management of one or more diseases disclosed herein are disclosed in the literature, e.g., *Physician's Desk Reference* ($56^{th}$ Ed., 2004), which is incorporated herein by reference.

6.3.2 Cycling Therapy

In some embodiments, the compound of the invention can be cyclically administered to a patient having the disease disclosed herein. Cycling therapy involves the administration of the compound of the invention for a period of time, followed by a rest for a period of time and repeating this sequential administration. Cycling therapy can reduce the development of resistance to one or more of the therapies, avoid or reduce the side effects of one of the therapies and/or improves the efficacy of the treatment.

Consequently, in one specific embodiment, the compound of the invention is administered daily in a single or divided doses in a four to six week cycle with a rest period of about a week or two weeks. The invention further allows the frequency, number and length of dosing cycles to be increased. Thus, another embodiment encompasses the administration of the compound of the invention for more cycles than are typical when it is administered alone. In yet another embodiment, the compound of the invention is administered for a greater number of cycles that would typically cause dose-limiting toxicity in a patient to whom a second active ingredient is not also being administered.

In some embodiments, (+)-2-[1-(3-ethoxy-4-methoxyphenyl)-2-methylsulfonylethyl]-4-acetylaminoisoindoline-1,3-dione is administered daily and continuously for three or four weeks at a dose of from about 10 to about 200 mg per day followed by a break of one or two weeks. In certain embodiments, cyclopropyl{2-[(1S)-1-(3-ethoxy-4-methoxyphenyl)-2-(methylsulfonyl)ethyl]-3-oxoisoindolin-4-yl}carboxamide is administered daily and continuously for three or four weeks at a dose of from about 10 to about 200 mg per day followed by a break of one or two weeks.

In another embodiment, the compound of the invention and a second active ingredient are administered orally, with administration of the compound of the invention occurring 30 to 60 minutes prior to a second active ingredient, during a cycle of four to six weeks. In another embodiment, the combination of the compound of the invention and a second active ingredient is administered by intravenous infusion over about 90 minutes every cycle. In one embodiment, one cycle comprises the administration of from about 0.1 to about 200 mg/day of the compound of the invention and from about 50 to about 200 mg/m²/day of a second active ingredient daily for three to four weeks and then one or two weeks of rest. In another embodiment, each cycle comprises the administration of from about 1 to about 30 mg/day of the compound of the invention and from about 50 to about 200 mg/m²/day of a second active ingredient for 3 to 4 weeks followed by one or two weeks of rest. Typically, the number of cycles during which the combinatorial treatment is administered to a patient will be from about one to about 24 cycles, more typically from about two to about 16 cycles and even more typically from about four to about three cycles.

The amount of the pharmaceutical composition administered according to the methods of the invention will depend on the subject being treated, the severity of the disorder or symptom of the disorder, the manner of administration, the frequency of administration and the judgment of the prescribing physician.

The frequency of administration is in the range of about an hourly dose to a monthly dose. In some embodiments, administration is from 8 times per day to once every other day or from 1 to 3 times per day. In one embodiment, a pharmaceutical composition of the invention is administered chronically, e.g., daily.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

6.4 Doses

In one embodiment, (+)-2-[1-(3-ethoxy-4-methoxyphenyl)-2-methylsulfonylethyl]-4-acetylaminoisoindoline-1,3-dione can be administered orally and in single or divided daily doses in an amount of from about 1 mg to about 1000 mg per day, given as a single once-a-day dose, preferably as divided doses throughout a day. More specifically, the daily dose of (+)-2-[1-(3-ethoxy-4-methoxyphenyl)-2-methylsulfonylethyl]-4-acetylaminoisoindoline-1,3-dione is administered twice daily in equally divided doses. Specifically, a daily dose range of (+)-2-[1-(3-ethoxy-4-methoxyphenyl)-2-methylsulfonylethyl]-4-acetylaminoisoindoline-1,3-dione can be from about 5 mg to about 500 mg per day, more specifically, between about 10 mg and about 200 mg per day. Specifically, the daily dose of (+)-2-[1-(3-ethoxy-4-methoxyphenyl)-2-methylsulfonylethyl]-4-acetylaminoisoindoline-1,3-dione may be administered in 5 mg, 10 mg, 15 mg, 20 mg, 25 mg, 30 mg, 50 mg, or 100 mg dosage forms. In managing the patient, the therapy should be initiated at a lower dose, perhaps about 1 mg to about 30 mg, and increased if necessary up to about 200 mg to about 1000 mg per day as either a single dose or divided doses, depending on the patient's global response. Specifically, (+)-2-[1-(3-ethoxy-4-methoxyphenyl)-2-methylsulfonylethyl]-4-acetylaminoisoindoline-1,3-dione may be administered in 10 mg, 20 mg, and 30 mg twice per day. Alternatively, (+)-2-[1-(3-ethoxy-4-methoxyphenyl)-2-methylsulfonylethyl]-4-acetylaminoisoindoline-1,3-dione may be administered in 40 mg once per day. Alternatively, the daily dose is from 0.01 mg/kg to 100 mg/kg.

In some embodiments, cyclopropyl{2-[(1S)-1-(3-ethoxy-4-methoxyphenyl)-2-(methylsulfonyl)ethyl]-3-oxoisoindolin-4-yl}carboxamide can be administered orally and in single or divided daily doses in an amount of from about 1 mg to about 1000 mg per day, given as a single once-a-day dose, preferably as divided doses throughout a day. More specifically, the daily dose of cyclopropyl{2-[(1S)-1-(3-ethoxy-4-methoxyphenyl)-2-(methylsulfonyl)ethyl]-3-oxoisoindolin-4-yl}carboxamide is administered twice daily in equally divided doses. Specifically, a daily dose range of cyclopropyl{2-[(1S)-1-(3-ethoxy-4-methoxyphenyl)-2-(methylsulfonyl)ethyl]-3-oxoisoindolin-4-yl}carboxamide can be from about 5 mg to about 500 mg per day, more specifically, between about 10 mg and about 200 mg per day. Specifically, the daily dose of cyclopropyl{2-[(1S)-1-(3-ethoxy-4-methoxyphenyl)-2-(methylsulfonyl)ethyl]-3-oxoisoindolin-4-yl}carboxamide may be administered in 5 mg, 10 mg, 15 mg, 20 mg, 25 mg, 30 mg, 50 mg, or 100 mg dosage forms. In managing the patient, the therapy should be initiated at a lower dose, perhaps about 1 mg to about 30 mg, and increased if necessary up to about 200 mg to about 1000 mg per day as either a single dose or divided doses, depending on the patient's global response. Specifically, cyclopropyl{2-[(1S)-1-(3-ethoxy-4-methoxyphenyl)-2-(methylsulfonyl)ethyl]-3-oxoisoindolin-4-yl}carboxamide may be administered in 10 mg, 20 mg, and 30 mg twice per day. Alternatively, the daily dose is from 0.01 mg/kg to 100 mg/kg.

Various dosage forms of the invention are discussed in section 5.5 below. In one embodiment, typical dosage forms of the invention comprise (+)-2-[1-(3-ethoxy-4-methoxyphenyl)-2-methylsulfonylethyl]-4-acetylaminoisoindoline-1,3-dione, or cyclopropyl{2-[(1S)-1-(3-ethoxy-4-methoxyphenyl)-2-(methylsulfonyl)ethyl]-3-oxoisoindolin-4-yl}carboxamide, in an amount from about 0.10 to about 1000 mg, from about 0.10 to about 800 mg, from about 0.10 to about 600 mg, from about 0.10 to about 500 mg, from about 0.10 to about 400 mg, from about 0.10 to about 300 mg, from about 0.10 to about 200 mg, or from about 0.10 to about 100 mg. In one embodiment, typical dosage forms comprise the compound in an amount of about 1, 2, 5, 10, 25, 30, 50, 100, 150, 200, 250, 300, 350, 400, 450, or 500 mg.

In one embodiment, typical dosage forms comprise the second active ingredient in an amount of 1 to about 1000 mg, from about 5 to about 500 mg, from about 10 to about 350 mg or from about 50 to about 200 mg. Of course, the specific amount of the agent will depend on the specific agent used, the type of disease or disorder being treated or managed, and the amount(s) of the compounds of the invention and any optional additional second active agents concurrently administered to the patient.

6.5 Pharmaceutical Compositions And Dosage Forms

Pharmaceutical compositions can be used in the preparation of individual, single unit dosage forms. Pharmaceutical compositions and dosage forms disclosed herein can comprise the compounds of the invention, or a pharmaceutically acceptable salt, solvate or stereoisomer thereof, and optionally a second active agent. Examples of the optional second active agents are disclosed herein (see, e.g., section 6.3.1). Pharmaceutical compositions and dosage forms disclosed herein can further comprise one or more carriers, excipients or diluents.

Single unit dosage forms disclosed herein are suitable for oral, mucosal (e.g., sublingual, nasal, vaginal, cystic, rectal, preputial, ocular, buccal or aural), parenteral (e.g., subcutaneous, intravenous, bolus injection, intramuscular or intraarterial), topical (e.g., eye drops or other ophthalmic preparations), transdermal or transcutaneous administration to a patient. Non-limiting examples of dosage forms include tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions or a water-in-oil liquid emulsions), solutions and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

Typical pharmaceutical compositions and dosage forms comprise one or more excipients. Suitable excipients are well known to those skilled in the art of pharmacy and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients can be accelerated by some excipients such as lactose or when exposed to water. Active ingredients that comprise primary or secondary amines are particularly susceptible to such accelerated decomposition. Consequently, this invention encompasses pharmaceutical compositions and dosage forms that contain little, if any, lactose or other mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the *U.S. Pharmacopeia* (USP) 25-NF20 (2002). In general, lactose-free compositions comprise active ingredients, a binder/filler and a lubricant in pharmaceutically compatible and pharmaceutically acceptable amounts. Particular lactose-free dosage forms comprise active ingredients, microcrystalline cellulose, pre-gelatinized starch and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Non-limiting examples of suitable packaging include hermetically sealed foils, plastics, unit dose containers (e.g., vials), blister packs and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers or salt buffers. Like the amounts and types of excipients, the amounts and specific types of active ingredients in a dosage form may differ depending on factors such as, but not limited to, the route by which it is to be administered to patients.

The invention further encompasses methods for treating, preventing and/or managing a disease selected from dermatomyositis, prurigo nodularis, pyoderma gangrenosum, alopecia areata, hidradenitis suppurtiva, rosacea, lichen planus, giant cell arteritis, Sjogren's syndrome, gout, chronic prostatitis, posterior uveitis, vulvodynia and interstitial cystitis by administering one or more pharmaceutical compositions and dosage forms disclosed herein to a patient having the disease.

6.5.1 Oral Dosage Forms

Pharmaceutical compositions disclosed herein that are suitable for oral administration can be presented as discrete dosage forms, such as, but are not limited to, tablets (e.g., chewable tablets), caplets, capsules and liquids (e.g., flavored syrups). Such dosage forms contain predetermined amounts of active ingredients and can be prepared by methods of pharmacy well known to those skilled in the art. See generally, *Remington's Pharmaceutical Sciences,* 18th ed., Mack Publishing, Easton Pa. (1990).

Typical oral dosage forms disclosed herein are prepared by combining the active ingredients in an intimate admixture with at least one excipient according to conventional pharmaceutical compounding techniques. Excipients can take a wide variety of forms depending on the form of preparation desired for administration. Non-limiting examples of excipients suitable for use in oral liquid or aerosol dosage forms include water, glycols, oils, alcohols, flavoring agents, preservatives and coloring agents. Non-limiting examples of excipients suitable for use in solid oral dosage forms (e.g., powders, tablets, capsules and caplets) include starches, sugars, microcrystalline cellulose, diluents, granulating agents, lubricants, binders and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers or both and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Non-limiting examples of excipients that can be used in the oral dosage forms disclosed herein include binders, fillers, disintegrants and lubricants. Non-limiting examples of binders suitable for use in pharmaceutical compositions and dosage forms include corn starch, potato starch or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose and mixtures thereof.

Non-limiting examples of suitable forms of microcrystalline cellulose include the materials sold as AVICEL-PH-101, AVICEL-PH-103 AVICEL RC-581, AVICEL-PH-105 (available from FMC Corporation, American Viscose Division, Avicel Sales, Marcus Hook, Pa.) and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Non-limiting examples of fillers suitable for use in the pharmaceutical compositions and dosage forms disclosed herein include talc, calcium carbonate (e.g., granules or powder), microcrystalline cellulose, powdered cellulose, dextrates, kaolin, mannitol, silicic acid, sorbitol, starch, pre-gelatinized starch and mixtures thereof. The binder or filler in pharmaceutical compositions disclosed herein is typically present in from about 50 to about 99 weight percent of the pharmaceutical composition or dosage form.

Disintegrants are used in the pharmaceutical compositions disclosed herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation and is readily discernible to those of ordinary skill in the art. Typical pharmaceutical compositions comprise from about 0.5 to about 15 weight percent of disintegrant, preferably from about 1 to about 5 weight percent of disintegrant.

Non-limiting examples of disintegrants that can be used in the pharmaceutical compositions and dosage forms disclosed herein include agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums and mixtures thereof.

Non-limiting examples of lubricants that can be used in the pharmaceutical compositions and dosage forms disclosed herein include calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laureate, agar and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.) and mixtures thereof. If used at all, lubricants are typically used in an amount of less than about 1 weight percent of the pharmaceutical compositions or dosage forms into which they are incorporated.

A particular solid oral dosage form of the invention comprises the compound of the invention (e.g., (+)-2-[1-(3-ethoxy-4-methoxyphenyl)-2-methylsulfonylethyl]-4-acetylaminoisoindoline-1,3-dione, or cyclopropyl{2-[(1S)-1-(3-ethoxy-4-methoxyphenyl)-2-(methylsulfonyl)ethyl]-3-oxoisoindolin-4-yl}carboxamide), anhydrous lactose, microcrystalline cellulose, polyvinylpyrrolidone, stearic acid, colloidal anhydrous silica and gelatin.

6.5.2 Delayed Release Dosage Forms

Active ingredients of the invention can be administered by controlled release means or by delivery devices that are well known to those of ordinary skill in the art. Non-limiting examples of controlled release means or delivery devices include those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556 and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency and increased patient compliance. In addition, controlled-release formulations can be used to affect the time of onset of action or other characteristics, such as blood levels of the drug and can thus affect the occurrence of side (e.g., adverse) effects.

Most controlled-release formulations are designed to initially release an amount of drug (active ingredient) that promptly produces the desired therapeutic effect and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water or other physiological conditions or compounds.

6.5.3 Parenteral Dosage Forms

Parenteral dosage forms can be administered to patients by various routes including, but not limited to, subcutaneous, intravenous (including bolus injection), intramuscular and intraarterial. Because their administration typically bypasses patients' natural defenses against contaminants, parenteral dosage forms are preferably sterile or capable of being sterilized prior to administration to a patient. Non-limiting examples of parenteral dosage forms include solutions ready for injection, dry products ready to be dissolved or suspended in a pharmaceutically acceptable vehicle for injection, suspensions ready for injection and emulsions.

Suitable vehicles that can be used to provide parenteral dosage forms of the invention are well known to those skilled in the art. Non-limiting examples of suitable vehicles include Water for Injection USP; aqueous vehicles such as, but not limited to, Sodium Chloride Injection, Ringer's Injection, Dextrose Injection, Dextrose and Sodium Chloride Injection and Lactated Ringer's Injection; water-miscible vehicles such as, but not limited to, ethyl alcohol, polyethylene glycol and polypropylene glycol; and non-aqueous vehicles such as, but not limited to, corn oil, cottonseed oil, peanut oil, sesame oil, ethyl oleate, isopropyl myristate and benzyl benzoate.

Compounds that increase the solubility of one or more of the active ingredients disclosed herein can also be incorporated into the parenteral dosage forms of the invention. For example, cyclodextrin and its derivatives can be used to increase the solubility of the compounds of the invention and its derivatives.

6.5.4 Topical, Transdermal And Mucosal Dosage Forms

Drugs can be applied locally to the skin and its adnexa or to a variety of mucous membranes. The routes that can be used include topical, transdermal, sublingual, nasal, vaginal, cystic, rectal, preputial, ocular, buccal or aural. Many dosage forms have been developed to deliver active principles to the site of application to produce local effects. Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non toxic and pharmaceutically acceptable. Moisturizers such as occlusives, humectants, emollients and protein rejuvenators can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Occlusives are substances that physically block water loss in the stratum corneum. Non-limiting examples of occlusives include petrolatum, lanolin, mineral oil, silicones such as dimethicone, zinc oxide and combinations thereof. Preferably, the occlusives are petrolatum and lanolin, more preferably petrolatum in a minimum concentration of 5%.

Humectants are substances that attract water when applied to the skin and theoretically improve hydration of the stratum corneum. However, the water that is drawn to the skin is water from other cells, not atmospheric water. With this type of moisturizer, evaporation from the skin can continue and actually can make the dryness worse. Non-limiting examples of humectants include glycerin, sorbitol, urea, alpha-hydroxy acids, sugars and combinations thereof. Preferably, the humectants are alpha hydroxy acids, such as glycolic acid, lactic acid, malic acid, citric acid and tartaric acid.

Emollients are substances that smooth skin by filling spaces between skin flakes with droplets of oil, and are not usually occlusive unless applied heavily. When combined with an emulsifier, they may help hold oil and water in the stratum corneum. Vitamin E is a common additive, which appears to have no effect, except as an emollient. Likewise, other vitamins, for example, A and D, are also added, but their effect is questionable. Non-limiting examples of emollients include mineral oil, lanolin, fatty acids, cholesterol, squalene, structural lipids and combinations thereof.

Protein rejuvenators are substances that rejuvenate the skin by replenishing essential proteins. Non-limiting examples of protein rejuvenators include collagen, keratin, elastin and combinations thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form may also be adjusted to improve delivery of one or more active ingredients. Similarly, the polarity of a solvent carrier, its ionic strength or tonicity can be adjusted to improve delivery. For example, absorption through the skin can also be enhanced by occlusive dressings, inunction or the use of dimethyl sulfoxide as a carrier. Compounds such as metal stearates (e.g., calcium stearate, zinc stearate, magnesium stearate, sodium stearate, lithium stearate, potassium stearate, etc.) can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant and as a delivery-enhancing or penetration-enhancing agent. Different salts, hydrates or solvates of the active ingredients can be used to further adjust the properties of the resulting composition.

6. EXAMPLES

Some embodiments are illustrated by the following non-limiting examples. The examples should not be construed as a limitation in the scope thereof. The scope of the invention is defined solely by the appended claims.

Example 1

Preparation of (+)-2-[1-(3-Ethoxy-4-Methoxyphenyl)-2-Methylsulfonylethyl]-4-Acetylaminoisoindoline-1,3-Dione [Compound (I)]

Preparation of 3-Aminophthalic acid. After a mixture of 10% Pd/C (2.5 g), 3-nitrophthalic acid (75.0 g, 355 mmol) and ethanol (1.5 L) was charged to a 2.5 L Parr hydrogenator under nitrogen, hydrogen was charged to the reaction vessel for up to 55 psi (379 kPa). The mixture was shaken for 13 hours while the hydrogen pressure was maintained at between 50 psi (245 kPa) and 55 psi (379 kPa). Hydrogen was released and the mixture was purged with nitrogen 3 times. The suspension was filtered through a celite bed and rinsed with methanol. The filtrate was concentrated in vacuum to yield a solid. The solid was suspended in ether and isolated by vacuum filtration. The solid was dried in vacuum to a constant weight to afford 54 g (84% yield) of 3-aminopthalic acid as a yellow product. The product in DMSO-$d_6$ was characterized by a $^1$H NMR spectrum showing the following chemical shifts (δ in ppm): 3.17 (s, 2H), 6.67 (d, 1H), 6.82 (d, 1H), 7.17 (t, 1H), 8-10 (brs, 2H). The product in DMSO-$d_6$ was characterized by a $^{13}$C-NMR spectrum showing the following chemical shifts (δ in ppm): 112.00, 115.32, 118.20, 131.28, 135.86, 148.82, 169.15, 170.09.

Preparation of 3-acetamidophthalic anhydride. A mixture of 3-aminophthalic acid (108 g, 596 mmol) and acetic anhydride (550 mL) was charged into a 1-L 3-necked round bottom flask equipped with a mechanical stirrer, a thermometer, and a condenser. The reaction mixture was refluxed for 3 hours, cooled to ambient temperature, and kept at 0-5° C. for another 1 hour. The crystalline solid was collected by vacuum filtration and washed with ether. The solid product was dried in vacuum at ambient temperature to a constant weight to yield 75 g (61% yield) of 3-acetamidopthalic anhydride as a white product. The product in CDCl$_3$ was characterized by a $^1$H NMR spectrum showing the following chemical shifts (δ in ppm): 2.21 (s, 3H), 7.76 (d, 1H), 7.94 (t, 1H), 8.42 (d, 1H), 9.84 (s, 1H).

Resolution of 2-(3-ethoxy-4-methoxyphenyl)-1-(methylsulphonyl)-eth-2-ylamine. A mixture of 2-(3-ethoxy-4-methoxyphenyl)-1-(methylsulphonyl)-eth-2-ylamine (137.0 g, 500 mmol), N-acetyl-L-leucine (52 g, 300 mmol), and methanol (1.0 L) was charged in a 3-L 3-necked round bottom flask equipped with a mechanical stirrer, a thermometer, and a condenser. After the reaction mixture was refluxed for 1 hour, the mixture was allowed to cool to ambient temperature and then stirred for another 3 hours at ambient temperature. The slurry was filtered and washed with methanol (250 L). The solid was air-dried and then dried in vacuum at ambient temperature to a constant weight, giving 109.5 g (98% yield) of the crude product (85.8% ee). The crude solid (55.0 g) and methanol (440 mL) were brought to reflux for 1 hour, cooled to room temperature and stirred for an additional 3 hours at ambient temperature. The slurry was filtered and the filter cake was washed with methanol (200 mL). The solid was air-dried and then dried in vacuum at 30° C. to a constant weight, yielding 49.6 g (90% recovery) of (S)-2-(3-ethoxy-4-methoxyphenyl)-1-(methylsulphonyl)-eth-2-ylamine-N-acetyl-L-leucine salt (98.4% ee). Chiral HPLC (1/99 EtOH/20 mM KH$_2$PO$_4$ @pH 7.0, Ultron Chiral ES-OVS from Agilent Technologies, 150 mm×4.6 mm, 0.5 mL/min., @240 nm): 18.4 min (S-isomer, 99.2%), 25.5 min (R-isomer, 0.8%).

Preparation of (+)-2-[1-(3-Ethoxy-4-methoxyphenyl)-2-methylsulfonylethyl]-4-acetylaminoisoindoline-1,3-dione. A 500 mL 3-necked round bottom flask was equipped with a mechanical stirrer, thermometer, and condenser. The reaction vessel was charged with (S)-2-(3-ethoxy-4-methoxyphenyl)-1-(methylsulphonyl)-eth-2-ylamine N-acetyl-L-leucine salt (25 g, 56 mmol, 98% ee), 3-acetamidophthalic anhydride (12.1 g 58.8 mmol), and glacial acetic acid (250 mL). The mixture was refluxed over night and then cooled to <50° C. After the solvent was removed in vacuum, the residue was dissolved in ethyl acetate. The resulting solution was washed with water (250 mL×2), saturated aqueous NaHCO$_3$ (250 mL×2), and brine (250 mL×2), and then dried over anhydrous sodium sulfate. After the solvent was evaporated in vacuum, the residue was recrystallized from a binary solvent containing a mixture of ethanol (150 mL) and acetone (75 mL). The solid was isolated by vacuum filtration and washed with ethanol (100 mL×2). The product was dried in vacuum at 60° C. to a constant weight, affording 19.4 g (75% yield) of (S)-{2-[1-(3-ethoxy-4-methoxyphenyl)-2-methylsulfonylethyl]-4-inoisoindoline-1,3-dione with 98% ee. Chiral HPLC (15/85 EtOH/20 mM KH$_2$PO$_4$ @pH 0.5, Ultron Chiral ES-OVS from Agilent Technology, 150 mm×4.6 mm, 0.4 mL/min., @240 nm): 25.4 min (S-isomer, 98.7%), 29.5 min (R-isomer, 1.2%). The product in CDCl$_3$ was characterized by a $^1$H NMR spectrum showing the following chemical shifts (6 in ppm): 1.47 (t, 3H), 2.26 (s, 3H), 2.87 (s, 3H), 3.68-3.75 (dd, 1H), 3.85 (s, 3H), 4.07-4.15 (q, 2H), 4.51-4.61 (dd, 1H), 5.84-5.90 (dd, 1H), 6.82-8.77 (m, 6H), 9.46 (s, 1H). The product in DMSO-$d_6$ was characterized by a $^{13}$C NMR spectrum showing the following chemical shifts (δ in ppm): 14.66, 24.92, 41.61, 48.53, 54.46, 55.91, 64.51, 111.44, 112.40, 115.10, 118.20, 120.28, 124.94, 129.22, 131.02, 136.09, 137.60, 148.62, 149.74, 167.46, 169.14, 169.48.

Example 2

Preparation of Cyclopropyl{2-[(1S)-1-(3-Ethoxy-4-Methoxyphenyl)-2-(Methylsulfonyl)Ethyl]-3-Oxoisoindolin-4yl}Carboxamide Cyclopropyl{2-[(1S)-1-(3-ethoxy-4-methoxyphenyl)-2-(methylsulfonyl)ethyl]-3-oxoisoindolin-4-yl}carboxamide was prepared according to the preparation procedure for Example 57 of U.S. Pat. No. 6,667,316. A stirred mixture of 7-amino-2-[(1S)-1-(3-ethoxy-4-methoxyphenyl)-2-(methylsulfonyl)ethyl]isoindolin-1-one (1.7 g, 4.2 mmol) and cyclopropanecarbonyl chloride (0.46 mL, 5.1 mmol) in tetrahydrofuran (10 mL) was heated to reflux for 15 minutes. To the mixture was added methanol (4 mL) at room temperature and the mixture was stirred for 10 minutes. The solvent was removed in vacuo to yield an oil. The oil was recrystallized from ethanol (20 mL) to give Compound (II) as a white solid (1.4 g, 71% yield); m.p. 172-174° C.; $^1$H NMR (CDCl$_3$) δ: 0.86-0.93 (m, 2H, 2CHH), 1.07-1.14 (m, 2H, 2CHH), 1.46 (t, J=6.9 Hz, 3H, CH$_3$), 1.63-1.73 (m, 1H, CH), 2.95 (s, 3H, CH$_3$), 3.68 (dd, J=4.4, 14.3 Hz, 1H, CHH), 3.86 (s, 3H, CH$_3$), 4.07 (q, J=7.1 Hz, 2H, CH$_2$), 4.20 (d, J=16.7 Hz, 1H, CHH), 4.21 (dd, J=9.9, 14.3 Hz, 1H, CHH), 4.44 (d, J=16.7 Hz, 1H, CHH), 5.73 (dd, J=4.3, 9.9 Hz, 1H, NCH), 6.84-7.02 (m, 4H, Ar), 7.44 (t, J=7.8 Hz, 1H, Ar), 8.43 (d, J=8.3 Hz, 1H, Ar), 10.46 (s, 1H, NH); $^{13}$C NMR (CDCl$_3$) δ: 8.24, 14.61, 16.10, 41.43, 47.81, 51.55, 55.75, 55.88, 64.56, 111.46, 112.09, 116.69, 116.99, 117.76, 119.17, 129.27, 133.54, 138.06, 141.22, 148.84, 149.67, 169.96, 172.59; Anal. Calcd. for C$_{24}$H$_{28}$N$_2$O$_6$S: C, 61.00; H, 5.97; N, 5.93. Found: C, 60.87; H, 6.13; N, 6.12.

Example 3

Tablets, each containing 50 milligrams of active ingredient, can be prepared in the following manner:

| Composition (for 1000 tablets) | |
|---|---|
| active ingredient | 50.0 grams |
| lactose | 50.7 grams |
| wheat starch | 7.5 grams |
| polyethylene glycol 6000 | 5.0 grams |
| talc | 5.0 grams |
| magnesium stearate | 1.8 grams |
| demineralized water | q.s. |

The solid ingredients are first forced through a sieve of 0.6 mm mesh width. The active ingredient, the lactose, the talc, the magnesium stearate and half of the starch then are mixed. The active ingredient is the compound of the invention, or a pharmaceutically acceptable salt, solvate or stereoisomer thereof. The other half of the starch is suspended in 40 milliliters of water and this suspension is added to a boiling solution of the polyethylene glycol in 100 milliliters of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

Example 4

Tablets, each containing 100 milligrams of active ingredient, can be prepared in the following manner:

| Composition (for 1000 tablets) | |
|---|---|
| active ingredient | 100.0 grams |
| lactose | 100.0 grams |
| wheat starch | 47.0 grams |
| magnesium stearate | 3.0 grams |

All the solid ingredients are first forced through a sieve of 0.6 mm mesh width. The active ingredient, the lactose, the magnesium stearate and half of the starch then are mixed. The other half of the starch is suspended in 40 milliliters of water and this suspension is added to 100 milliliters of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

Example 5

Tablets for chewing, each containing 75 milligrams of active ingredient, can be prepared in the following manner:

| Composition (for 1000 tablets) | |
|---|---|
| active ingredient | 75.0 grams |
| mannitol | 230.0 grams |
| lactose | 150.0 grams |
| talc | 21.0 grams |
| glycine | 12.5 grams |
| stearic acid | 10.0 grams |
| saccharin | 1.5 grams |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. The active ingredient, the glycine and the saccharin are carefully mixed. The mannitol, the lactose granulate, the stearic acid and the talc are added and the whole is mixed thoroughly and compressed to form tablets of approximately 10 mm diameter which are concave on both sides and have a breaking groove on the upper side.

Example 6

Tablets, each containing 10 milligrams of active ingredient, can be prepared in the following manner:

| Composition (for 1000 tablets) | |
|---|---|
| active ingredient | 10.0 grams |
| lactose | 328.5 grams |
| corn starch | 17.5 grams |
| polyethylene glycol 6000 | 5.0 grams |
| talc | 25.0 grams |
| magnesium stearate | 4.0 grams |
| demineralized water | q.s. |

The solid ingredients are first forced through a sieve of 0.6 mm mesh width. Then the active ingredient, lactose, talc, magnesium stearate and half of the starch are intimately mixed. The other half of the starch is suspended in 65 milliliters of water and this suspension is added to a boiling solution of the polyethylene glycol in 260 milliliters of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

Example 7

Gelatin dry-filled capsules, each containing 100 milligrams of active ingredient, can be prepared in the following manner:

| Composition (for 1000 capsules) | |
|---|---|
| active ingredient | 100.0 grams |
| microcrystalline cellulose | 30.0 grams |
| sodium lauryl sulphate | 2.0 grams |
| magnesium stearate | 8.0 grams |

The sodium lauryl sulphate is sieved into the active ingredient through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 milligrams each into size 0 (elongated) gelatin dry-fill capsules.

Example 8

A 0.2% injection or infusion solution can be prepared, for example, in the following manner:

| Composition | |
|---|---|
| active ingredient | 5.0 grams |
| sodium chloride | 22.5 grams |
| phosphate buffer pH 7.4 | 300.00 grams |
| demineralized water | to 2500.0 milliliters |

The active ingredient is dissolved in 1000 milliliters of water and filtered through a microfilter. The buffer solution is added and the whole is made up to 2500 milliliters with water. To prepare dosage unit forms, portions of 1.0 or 2.5 milliliters each are introduced into glass ampoules (each containing respectively 2.0 or 5.0 milligrams of active ingredient).

Example 9

An ointment for topical use can be prepared, for example, in the following manner:

| Composition | |
|---|---|
| active ingredient | 10 g |
| petrolatum | 80 g |
| mineral oil | 120 g |
| 2% saline solution | 2 L |
| triamcinolone acetonide | 0.5 g |

The above ingredients are mixed uniformly to form an ointment using a conventional mixer or homogenizer, by shaking or by ultrasonic energy.

Example 10

A gel for topical use can be prepared, for example, in the following manner:

| Composition | |
|---|---|
| active ingredient | 10 g |
| Carboxylmethyl cellulose | 0.2 g |
| Glycerin | 40.0 g |
| 0.4 mole/L Citrate buffer | 25.0 g |
| Distilled water | to 100 g |

The above ingredients are mixed uniformly to form a gel using a conventional mixer or homogenizer, by shaking or by ultrasonic energy.

Example 11

A paste for topical use can be prepared, for example, in the following manner:

| Composition | |
|---|---|
| active ingredient | 10 g |
| Carboxymethyl cellulose | 2.0 g |
| Glycerin | 25.0 g |
| Cetanol | 2.8 g |
| Glyceryl monostearate | 9.3 g |
| Tween 80 | 2.0 g |
| Glucuronic acid | 1.0 g |
| 0.4 mole/l Citrate buffer | 20.0 g |
| Distilled water | to 100 g |

The above ingredients are mixed uniformly to form a paste using a conventional mixer or homogenizer, by shaking or by ultrasonic energy.

Example 12

A liquid composition for topical use can be prepared, for example, in the following manner:

| Composition | |
|---|---|
| active ingredient | 10 g |
| Carboxymethyl cellulose | 0.1 g |
| Glycerin | 15.0 g |
| 0.4 mole/l Citrate buffer (pH 4.5) | 50.0 g |
| Distilled water | to 100 g |

The solid ingredients are dispersed/dissolved in the liquid ingredients uniformly to form a liquid using a conventional mixer or homogenizer, by shaking or by ultrasonic energy.

Example 13

A spray for topical use can be prepared, for example, in the following manner:

| Composition | |
|---|---|
| The liquid composition of Example 12 | 100.0 g |
| Freon 114 | 100.0 g |

The liquid composition and Freon 114 are filled into Teflon-coated aluminum spray containers.

Example 14

Effect of Compound (II) on Keratinocyte MxA and Cytokeratin Levels

A) Materials.

Human leukocyte units (buffy coat) were obtained from healthy blood donors (Blood Center of New Jersey, East Orange, N.J., USA). Hank's Buffered Salt Solution (HBSS) was obtained from VWR Scientific (Radnor, Pa.). Ficoll-Paque Plus was obtained from Amersham Bioscience (Cat #17-1440-02). Cells were grown in complete medium consisting of Roswell Park Memorial Institute (RPMI-1640), 5% human serum, 100 U.mL$^{-1}$ penicillin, 100 mg mL$^{-1}$ streptomycin, 2 mM L-glutamine (components from VWR Scientific). Plasmacytoid dendritic cells (pDCs) were purchased from AllCells (Cat # PB013). CpG-A ODN 2216 oligonucleotide (TLR9 agonist) was obtained from InvivoGen. Adult human epidermal keratinocytes (HEKa) were obtained from ScienCell (Cat #2110). Primary antibodies to MxA were obtained from Novus Biologicals, and Cytokeratin antibody was obtained from Invitrogen. Secondary antibodies namely Alexa-labelled anti-goat and anti-rabbit fluorescein (IgG1) or TRITC-conjugated (IgG) antibodies were obtained from Invitrogen. Cell nuclei were stained with DAPI or 4',6-diamidino-2-phenylindole from Invitrogen. Compound (II) was obtained according to the preparation procedures disclosed herein.

B) Methods.

PBMC Purification.

Human leukocytes (50 mL) were divided into two 25 mL aliquots and added into two 50 mL conical tubes containing 25 mL of sterile HBSS. The tubes were gently mixed by inverting several times. Ficoll-Paque Plus (15 mL) at room temperature was aliquoted into four 50 mL conical tubes. Then the buffy coat/HBSS mixture (25 mL) was gently and slowly layered on top of the Ficoll-Paque Plus. The samples were centrifuged with Eppendorf Centrifuge 5810R (Rotor A-4-81) at 450 rpm for 35 minutes. The top layer containing plasma was discarded. The interface containing mononuclear cells was transferred into two 50 mL conical tubes. Both conical tubes were filled to total volume of 50 mL with HBSS and centrifuged at 1200 rpm for 10 minutes. The cells were washed again in HBSS and centrifuged at 1000 rpm for 10 minutes. Human red blood cell lysis buffer (5 mL) was added to the cell pellets and incubated for 5 minutes at room temperature. Phosphate buffered saline (45 mL) was added to the conical tubes and centrifuged at 1200 rpm for 10 minutes. The cell pellets were combined and resuspended in 20 mL complete medium and the cells were counted.

Human pDC/HEKa Coculture.

The Human pDC/HEKa Coculture involves stimulation with CpG-A oligodeoxynucleotide 2216. The CpG-A stimulation would induce pDCs to secrete interferon-alpha (IFN-$\alpha$) which in turn elicits increased expression of MxA protein from keratinocytes. HEKa were plated in 6-well plates at density of $1 \times 10^5$ cells/well and incubated overnight in a defined keratinocyte medium. The medium was removed in the next day and then $1.8 \times 10^5$ pDC cells, in defined pDC medium, were overlaid on the HEKa cells. Compound (II) was added to the medium to obtain final concentrations of 0.25 µM, 0.5 µM, 1 µM and 2 µM. One hour after the addition of Compound (II), CpG-A was added to each of these concentrations and then incubated overnight.

The cells were fixed and immunostained the co-cultures with antibodies to keratinocyte myxovirus resistance protein A (MxA) and Cytokeratin as follows using the ThermoScientific Cellomics High Content Screening (HCS) Readers using vHCS Scan Software.

Eighteen hours after the addition of Compound (II), cocultures were fixed for 30 minutes with BD fixation/permeabilization buffer, washed, and blocked with 2% normal goat serum/bovine serum albumin solution for an hour. Cocultures were then incubated overnight with primary antibodies to MxA and Cytokeratin. Cells were washed and incubated for an hour with Alexa anti-goat and anti-rabbit fluorescein (IgG1) or TRITC-conjugated (IgG) secondary antibodies. Nuclei were stained with DAPI or 4',6-diamidino-2-phenylindole. Cocultures were washed and incubated in 1X phosphate buffered saline (PBS) and plates scanned using Thermo Scientific ArrayScan VTI HCS Reader, a modular High Content Screening instrument designed for high-capacity automated fluorescence imaging and quantitative analysis of fixed and live cells. The output was analyzed using Cellomics Compartmental Analysis algorithm to quantitate fluorescence levels in the green and red channels. Data was exported to Microsoft Excel worksheets. Mean fluorescence intensity levels of MxA and Cytokeratin of the samples were expressed as percentage of mean fluorescence intensity levels of MxA and cytokeratin of Example A1. Histograms were generated and statistical analysis was performed using GraphPad Prism v4.0 (GraphPad Software, Inc., San Diego, Calif.).

Figure 2:
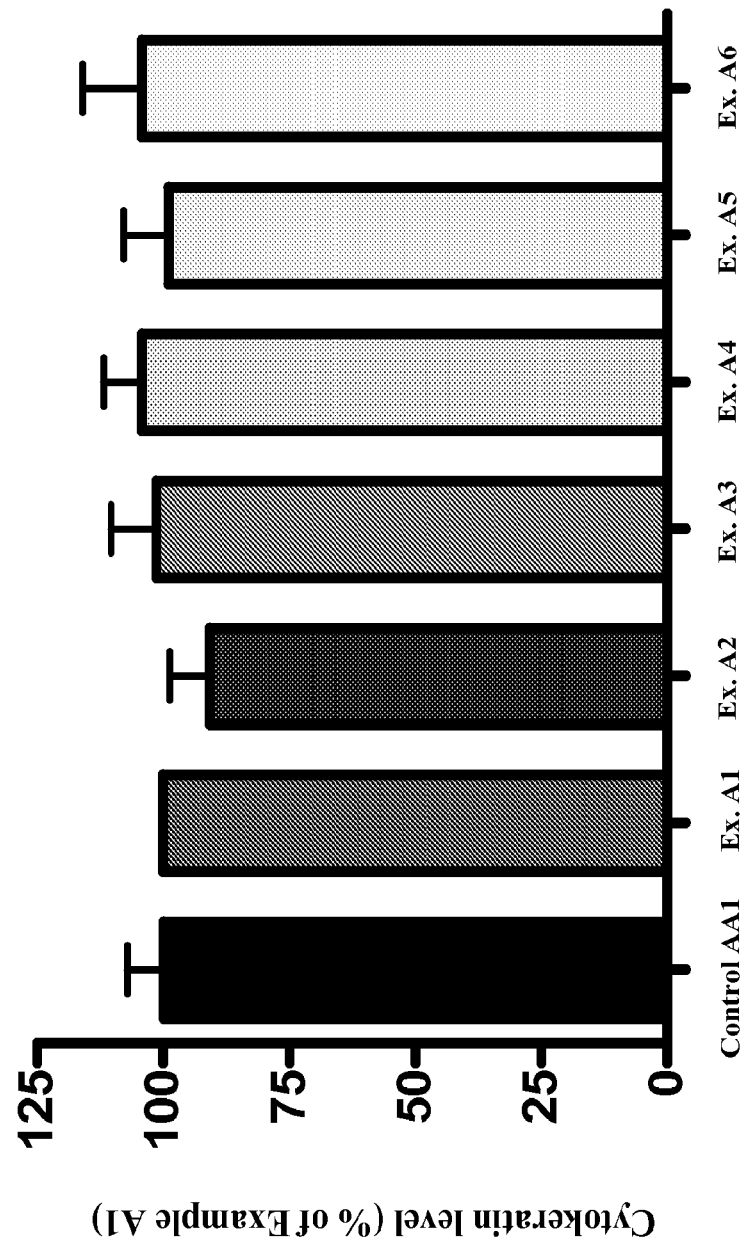
FIG. 2 illustrates the cytokeratin levels of different samples including Control AA1 and Examples A1-A6 used in Example 14.

FIGS. 1-2 show the levels of keratinocyte MxA and cytokeratin of the samples averaged from four independent experiments relative to the keratinocyte MxA and cytokeratin levels of Example A1 with pDCs derived from separate donors. The sample without CpG-A stimulation and cultured in the presence of plasmacytoid dendritic cells (pDCs) is labeled as Control AA1; the sample with CpG-A stimulation and cultured in the presence of pDCs is labeled as Example A1; the samples with CpG-A stimulation and Compound (II) (0.25 µM, 0.5 µM, 1 µM and 2 µM) and cultured in the presence of pDCs are labeled as Examples A2-A5 respectively; and the sample with CpG-A stimulation and cultured in the absence of pDCs is labeled as Example A6.

Referring to FIGS. 1-2, one asterisk * refers to $p<0.05$; two asterisks  refers to $p<0.01$; and three asterisks * refers to $p<0.0001$, as determined by one-way ANOVA followed by Bonferroni's multiple comparison post-hoc test comparing keratinocyte MxA and cytokeratin levels of samples with keratinocyte MxA and cytokeratin level of Example A1.

FIG. 1 shows the mean keratinocyte MxA level of Example A1 is nearly double of the mean keratinocyte MxA level of Control AA1. Toll-like receptor 9 (TLR-9) stimulation (CpG-A stimulation) via CpG-A oilgonucleotide was used for stimulating the release of interferon-alpha (IFN-$\alpha$) from pDCs. The sample with CpG-A stimulation (Example A1) induced nearly a 2-fold increase in the keratinocyte MxA level compared with the control experiment (Control AA1).

The keratinocyte MxA levels remained unchanged when the adult human epidermal keratinocytes cultured in the absence of pDCs, were stimulated with CpG-A oilgonucleotide (Example A6). Compound (II) induced a decrease in the keratinocyte MxA protein levels by 19% at 0.25 µM and 39% at 0.5 µM of Compound (II). Compound (II) decreased keratinocyte MxA levels by 29% at 1 µM and 40% at 2 µM of Compound (II).

FIG. 2 shows the cytokeratin level of the samples relative to that of Example A1. Compound (II) had no effect on the cytokeratin levels on the keratinocytes. These results (FIGS. 1-2) show that the phosphodiesterase-4 (PDE4) inhibitor, Compound (II) can selectively inhibit the keratinocyte MxA levels and therefore has the potential to modulate IFN-$\alpha$ induced pathophysiology.

Example 15

Comparison Between JNK Inhibitor, PDE4 Inhibitors and Antimalarial Chloroquine on Inhibiting the Production of IFN-$\alpha$ and TNF-$\alpha$ A) Materials.

Compound (I) and Compound (II) were obtained according to the preparation procedures disclosed herein. Antimalarial chloroquine (Cat # C6628-25G) was obtained from Sigma Chemical Co. JNK inhibitor CC-930 was obtained according to known procedures.

B) Methods.

The IFN-$\alpha$ and TNF-$\alpha$ levels were measured by enzyme-linked immunoabsorbant assay (ELISA) obtained from R&D System, Minneapolis, Minn., known as Human IFN-alpha ELISA Kit (PBL Interferon Source, Cat #41100-1) and Human TNF-alpha Quantikine ELISA Kit (ThermoScientific, Cat # EH3TNFA5) respectively.

Human PBMCs ($1 \times 10^5$ cells) or pDCs ($1.5 \times 10^5$ cells) were plated in 96-well plates in RPMI media containing either 10% FBS (PBMCs) or 5% FBS (pDCs). Compounds were diluted with DMSO (PBMCs) or media (pDCs) from a 4 mM stock of each compound to obtain different concentrations. Human PBMCs or pDCs were pretreated with different concentrations of compounds for an hour prior stimulation. Cells were then stimulated with 1 µM (PBMCs) or 10 µM (PDCs) CpG-A ODN 2216 for 18 hours.

The samples with Compound (II) (0.25 µM, 0.5 µM and 1 µM) are labeled as Examples B1-B3; the samples with Compound (I) (0.25 µM, 0.5 µM and 1 µM) are labeled as Examples B4-B6; the samples with CC-930 (1.0 µM, 2.0 µM and 3.0 µM) are labeled as Examples B7-B9; and the samples with chloroquine (0.5 µM, 1.0 µM and 2.0 µM) are labeled as Examples B10-B12. Keratinocytes of samples (Examples B1-B12) cultured in the presence of pDCs were stimulated with CpG-A oligonucleotide.

Two control experiments were done. The first control experiment (Control BB1) was done with similar procedures mentioned-above but without CpG-A stimulation and without the addition of inhibitors. The second control experiment (Control BB2) was done with similar procedures mentioned-above but without the addition of inhibitors.

Supernatant was collected after 18 hours. IFN-α and TNF-α levels were assayed by ELISA according to manufacturer's instructions.

Figure 3:
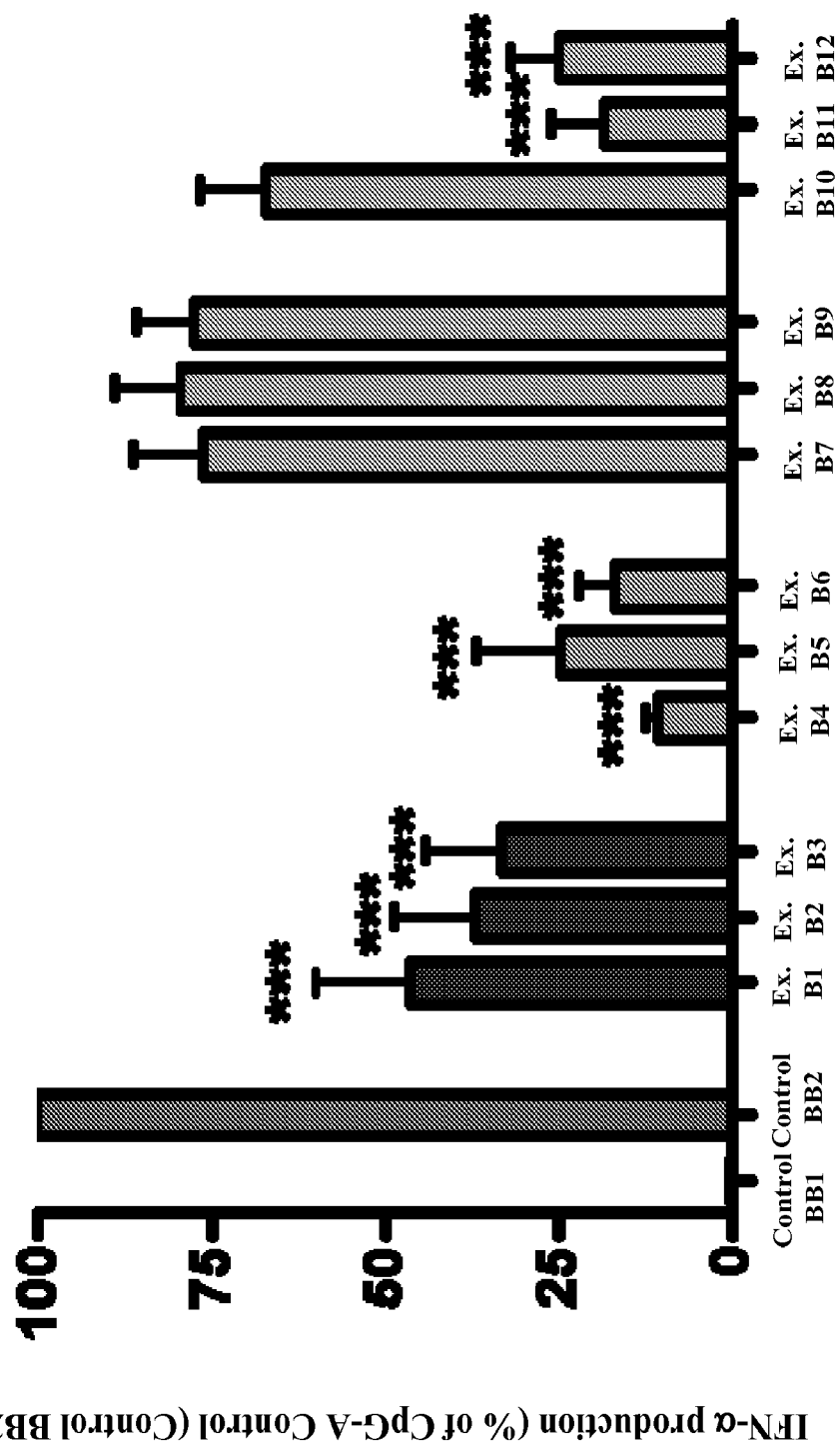
FIG. 3 illustrates the IFN-α production of different samples including Controls BB1-BB2 and Examples B1-B12 used in Example 15.
Figure 4:
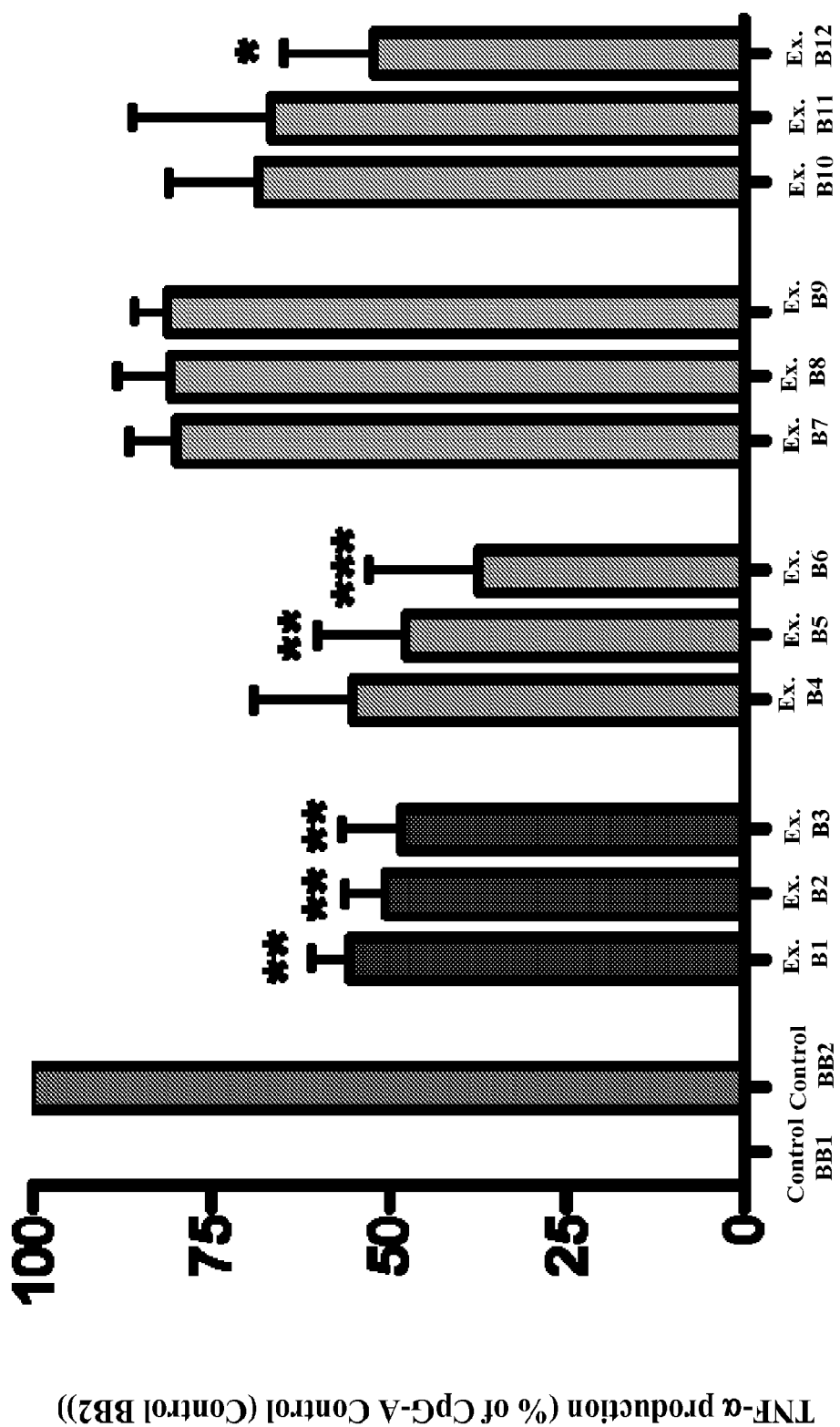
FIG. 4 illustrates the TNF-α production of different samples including Controls BB1-BB2 and Examples B1-B12 used in Example 15.

FIGS. 3-4 show the experimental results of the IFN-α ELISA and TNF-αELISA of samples.

Referring to FIGS. 3-4, one asterisk * refers to p<0.05; two asterisks  refers to p<0.01; three asterisks * refers to p<0.0001, as determined by one-way ANOVA followed by Bonferroni's multiple comparison post-hoc test comparing the IFN-α and TNF-α levels of samples with the IFN-α and TNF-α levels of Control BB2.

Charts shown in FIGS. 3-4 were obtained from 4 independent IFN-α experiments and 2 independent TNF-α ELISA experiments. Compound (II) (Examples B1-B3) and Compound (I) (Examples B4-B6) inhibited the production of IFN-α (P<0.0001) and TNF-α relative to CpG-A stimulation (Control BB2). CC-930 (Examples B7-B9) induced an approximately 25% inhibition of the production of IFN-α and TNF-α, which is lower than using Compound (I) and Compound (II), relative to CpG-A stimulation (Control BB2). Chloroquine (Examples B10-B12) induced an approximately 75% inhibition of the production of IFN-α at 1.0 µM and 2.0 µM concentrations of chloroquine and induced an approximately 50% inhibition of the production of TNF-α at 2 µM of chloroquine.

Example 16

Effect of JNK Inhibitor, PDE4 Inhibitors and Antimalarial Chloroquine on Keratinocyte MxA and Cytokeratin in the PDC-Keratinocyte Co-Culture A) Materials.

Compound (I) and Compound (II) were obtained according to the preparation procedures disclosed herein. Antimalarial chloroquine was obtained from Sigma Chemical Co. (Cat # C6628-25G). JNK inhibitor CC-930 was obtained according to known procedures.

B) Methods.

The Human pDC/HEKa Coculture involves stimulation with CpG-A oligodeoxynucleotide. CpG-A-stimulation would induce pDCs to secrete interferon-alpha (IFN-α) which in turn elicits increased expression of MxA protein from keratinocytes. HEKa were plated in 6-well plates at density of $1 \times 10^5$ cells/well and incubated overnight in a defined keratinocyte medium. The medium was removed in the next day and then $1.8 \times 10^5$ pDC cells, in defined pDC medium, were overlaid on the HEKa cells. Compound (II) was added to the medium to obtain final concentrations of 0.25 µM, 0.5 µM and 1 µM. One hour after the addition of Compound (II), CpG-A was added to each of the concentrations and then incubated overnight. Same samples from Example 15 were used here.

The cells were fixed and immunostained the co-cultures with antibodies to keratinocyte myxovirus resistance protein A (MxA) and Cytokeratin as follows using the ThermoScientific Cellomics High Content Screening (HCS) Readers using vHCS Scan Software.

Eighteen hours after the addition of Compound (II), cocultures were fixed for 30 minutes with BD fixation/permeabilization buffer, washed, and blocked with 2% normal goat serum/bovine serum albumin solution for an hour. Cocultures were then incubated overnight with primary antibodies to MxA and Cytokeratin. Cells were washed and incubated for an hour with Alexa anti-goat and anti-rabbit fluorescein (IgG1) or TRITC-conjugated (IgG) secondary antibodies. Nuclei were stained with DAPI or 4',6-diamidino-2-phenylindole. Cocultures were washed and incubated in 1X phosphate buffered saline (PBS) and plates scanned using Thermo Scientific ArrayScan VTI HCS Reader, a modular High Content Screening instrument designed for high-capacity automated fluorescence imaging and quantitative analysis of fixed and live cells. The output was analyzed using Cellomics Compartmental Analysis algorithm to quantitate fluorescence levels in the green and red channels. Data was exported to Microsoft Excel worksheets. Mean fluorescence intensity levels of MxA and Cytokeratin of the samples were expressed as percentage of mean fluorescence intensity levels of MxA and cytokeratin of Control BB2.

Figure 5:
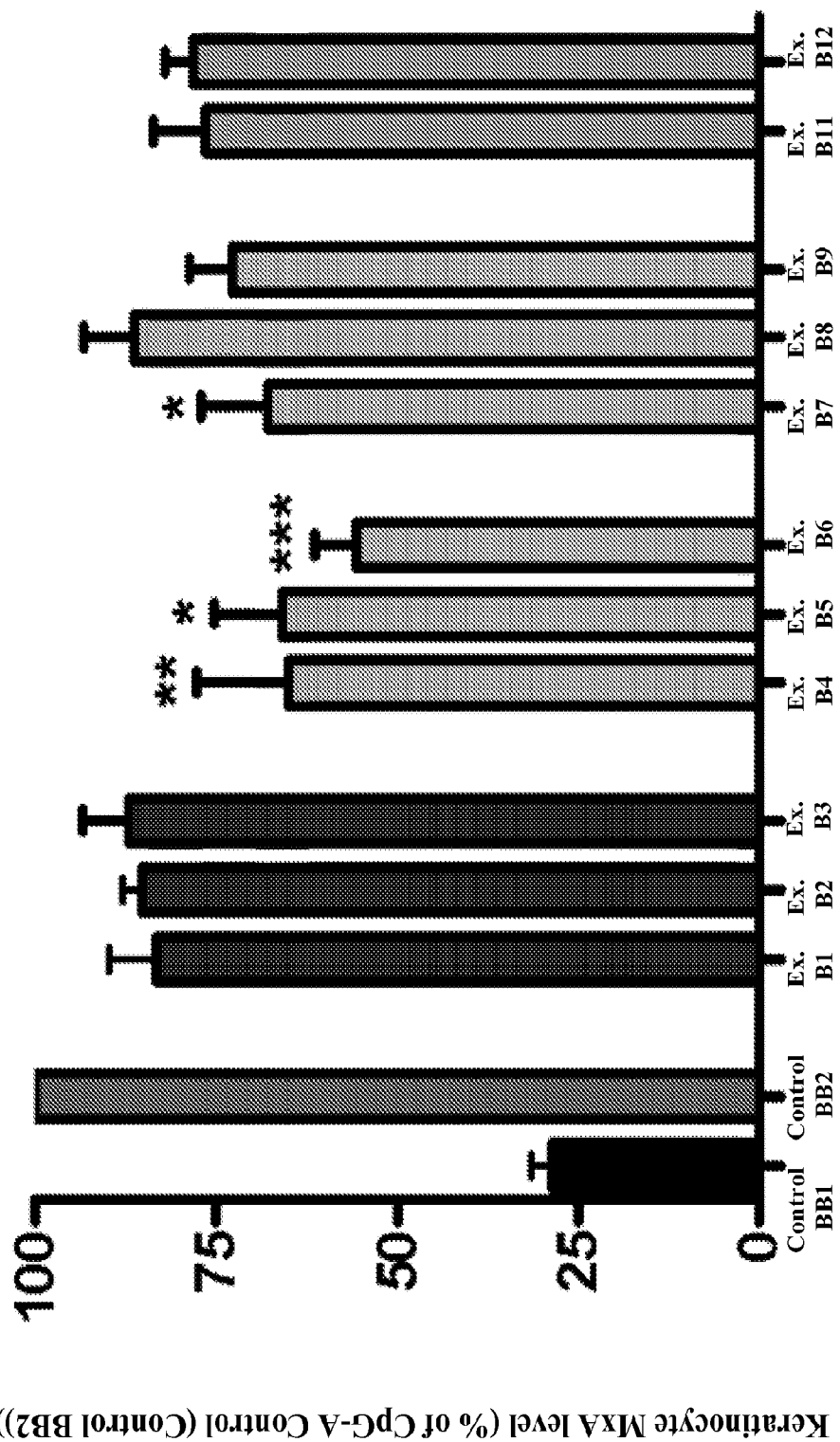
FIG. 5 illustrates the keratinocyte MxA levels of different samples including Controls BB1-BB2 and Examples B1-B9 and B11-B12 used in Example 16.
Figure 6:
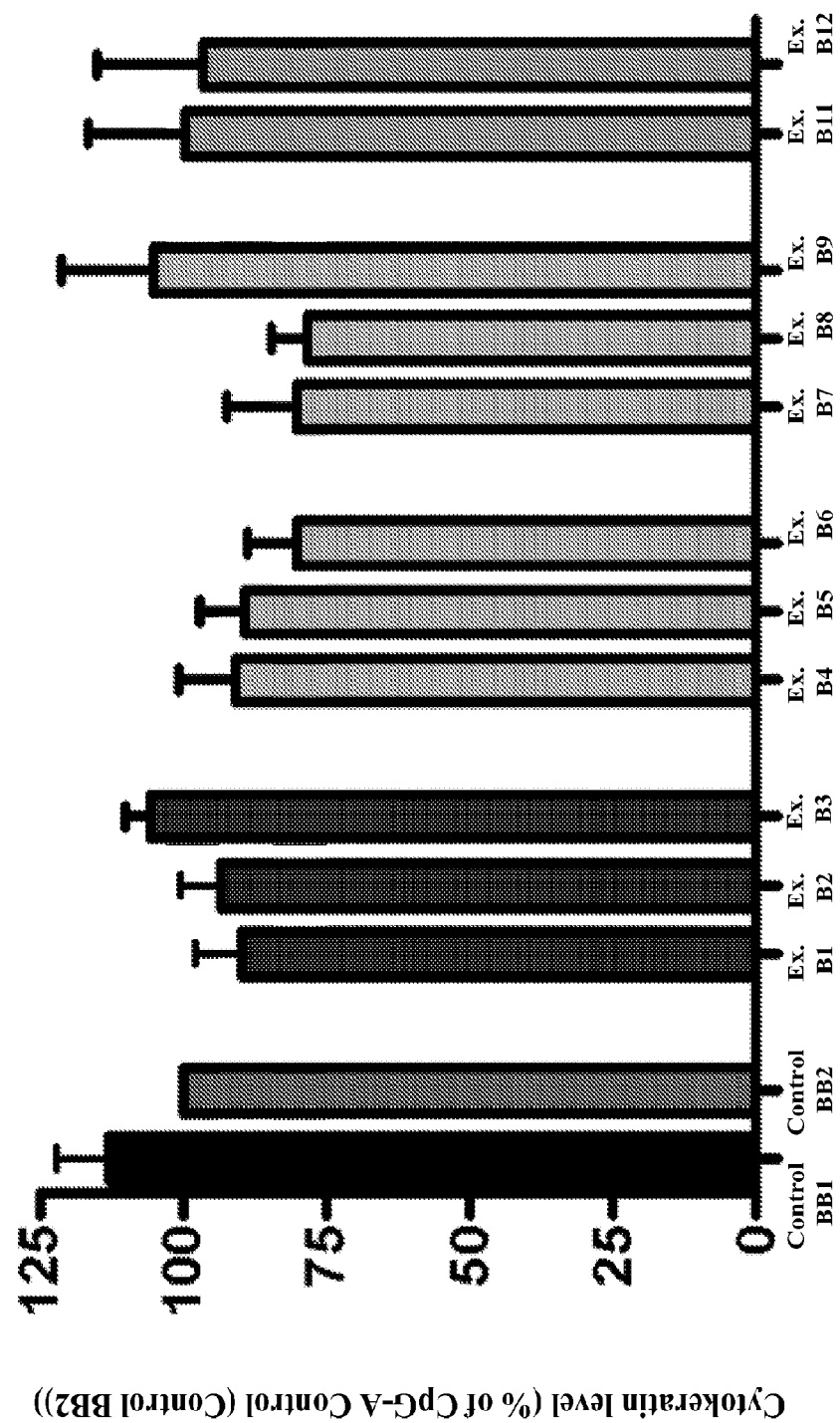
FIG. 6 illustrates the cytokeratin levels of different samples including Controls BB1-BB2 and Examples B1-B9 and B11-B12 used in Example 16.

The levels of keratinocyte MxA and cytokeratin of the samples shown in FIGS. 5-6 were obtained from 4 independent experiments.

Referring to FIGS. 5-6, one asterisk * refers to p<0.05; two asterisks  refers to p<0.01; and three asterisks * refers to p<0.0001, as determined by one-way ANOVA followed by Bonferroni's multiple comparison post-hoc test comparing keratinocyte MxA and cytokeratin levels of samples with keratinocyte MxA and cytokeratin level of Control BB2.

CpG-A stimulation (Control BB2) induced nearly a 4-fold increase in keratinocyte MxA levels relative to DMSO (Control BB1). Among the compounds tested, Compound (I) (Examples B4-B6) has the greatest ability to inhibit the production of the keratinocyte MxA. CC-930 (Examples B7-B9) showed a 32% decrease in the keratinocyte MxA level at 1 µM of CC-930 (which was statistically significant by one-way ANOVA (P<0.05)) while Compound (II) showed a 13-15% decrease in the keratinocyte MxA level.

Although a result of decreasing keratinocyte MxA levels by Compound (II) at 0.5 µM was shown in Example 14, it is possible that donor to donor pDC variability may be attritutable to the lack of significant effect of Compound (II). Since Compound (I) and Compound (II) efficiently inhibited the production of IFN-α and TNF-α, it is likely that the IFN-α inducible genes are modulated by PDE4 inhibition. Cytokeratin mean fluorescence intensity was also measured in Example 14 as a marker of keratinocytes.

Compound (II), Compound (I) and CC-930 had no significant effect on the keratinocyte cytokeratin, indicating that the compounds did not indiscriminately suppress the production of keratinocyte protein.

Example 17

Examination of Type 1 IFN Signature in PBMC

IFN-α Production in CpG-A Stimulated Human PBMC

Seven donors were used in the gene expression experiments. These donors were examined for the IFN-α protein levels (pg/mL) from the CpG-A stimulated peripheral blood mononuclear cells (hPBMCs) by the IFN-α ELISA.

A) Materials.

Human leukocyte units (buffy coat) were obtained from healthy blood donors (Blood Center of New Jersey, East Orange, N.J., USA). Hank's Buffered Salt Solution (HBSS) was obtained from VWR Scientific (Radnor, Pa.). Ficoll- Paque Plus was obtained from Amersham Bioscience (Cat#17-1440-02). Cells were grown in complete medium consisting of Roswell Park Memorial Institute (RPMI-1640), 5% human serum, 100 U·mL$^{-1}$ penicillin, 100 mg mL$^{-1}$ streptomycin, 2 mM L-glutamine (components from VWR Scientific). CpG-A ODN 2216 oligonucleotide (TLR9 agonist) was obtained from InvivoGen). RNeasy Mini Kit for RNA preparation was obtained from Qiagen (Cat #74104). Taqman reverse transcriptase enzyme was obtained from Applied Biosystems (Cat # N808-0234). Pre-made TaqMan® Gene Expression Assays for MX1, IRF-7, OAS1, OASL, CXCL9 (MIG), CXCL10 (IP-10), CXCL11, STAT1, IFIT1, MCP1, PLSCR1, XIAPAF1, IFI44, MX2, OAS2 and LY6E were purchased from Applied Biosystems.

B) Methods.

PBMC Purification.

Human leukocytes (50 mL) were divided into two 25 mL aliquots and added into two 50 mL conical tubes containing 25 mL of sterile HBSS. The tubes were gently mixed by inverting several times. Ficoll-Paque Plus (15 mL) at room temperature was aliquoted into four 50 mL conical tubes. Then the buffy coat/HBSS mixture (25 mL) was gently and slowly layered on top of the Ficoll-Paque Plus. The samples were centrifuged with Eppendorf Centrifuge 5810R (Rotor A-4-81) at 450 rpm for 35 minutes. The top layer containing plasma was discarded. The interface containing mononuclear cells was transferred into two 50 mL conical tubes. Both conical tubes were filled to total volume of 50 mL with HBSS and centrifuged at 1200 rpm for 10 minutes. The cells were washed again in HBSS and centrifuged at 1000 rpm for 10 minutes. Human red blood cell lysis buffer (5 mL) was added to the cell pellets and incubated for 5 minutes at room temperature. Phosphate buffered saline (45 mL) was added to the conical tubes and centrifuged at 1200 rpm for 10 minutes. The cell pellets were combined and resuspended in 20 mL complete medium and the cells were counted.

Human PBMCs ($1 \times 10^5$ cells) were plated in 96-well plates in RPMI media containing 10% FBS. Some cells were then stimulated with CpG-A ODN 2216 (1 μM) for 18 hours. Some cells were not stimulated with CpG-A ODN 2216. Supernatant was collected after 18 hours. IFN-α and TNF-α levels were assayed by IFN-alpha ELISA Kit and TNF-alpha Quantikine ELISA Kit according to manufacturer's instructions.

The samples from Donors 1, 2, 3, 4, 5, 6 and 7 with CpG-A stimulation are labeled as Examples D2, D4, D6, D8, D10, D12 and D14 respectively; whereas the samples from Donors 1, 2, 3, 4, 5, 6 and 7 without CpG-A stimulation are labeled as Examples D1, D3, D5, D7, D9, D11 and D13 respectively.

Figure 7:
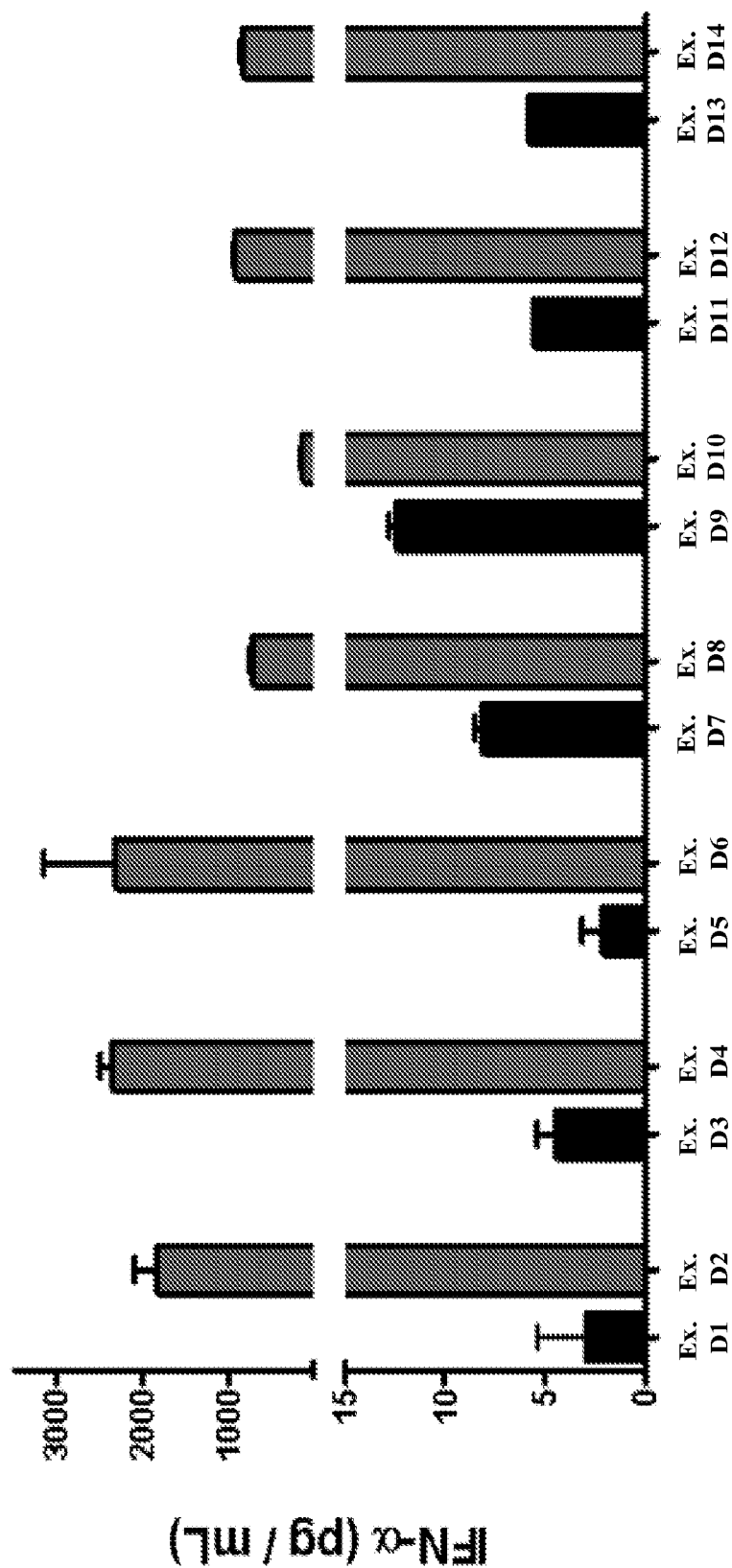
FIG. 7 illustrates the concentration of IFN-α (pg/mL) of different samples including Examples D1-D14 used in Example 17.

FIG. 7 shows there are 10- to 1000-fold increase in the IFN-α levels in 7 donors' PBMCs upon CpG-A stimulation (i.e., Examples D2, D4, D6, D8, D10, D12 and D14) compared with the samples without CpG-A stimulation (i.e., Examples D1, D3, D5, D7, D9, D11 and D13). Different scale of the y-axis of the chart shown in FIG. 7 are used to plot the samples with and without CpG-A stimulation in order to demonstrate the difference in the concentration of IFN-α.

Example 18

Examination of Type 1 IFN Signature in PBMC

Effect of Compounds on Inhibiting the Production of IFN-α in CpG-A Stimulated hPBMC A) Materials.

Compound (I) and Compound (II) were obtained according to the preparation procedures disclosed herein. Antimalarial chloroquine (Cat # C6628-25G), Chloroquine (Cat # C6628-25G) and Hydroxychloroquine (Cat # H0915) were obtained from Sigma Chemical Co., St. Louis, Mo. Quinacrine (Cat # Q8133) was obtained from LKT laboratories. JNK inhibitor CC-930 was obtained according to known procedures.

B) Methods.

PBMC Purification.

Human leukocytes (50 mL) were divided into two 25 mL aliquots and added into two 50 mL conical tubes containing 25 mL of sterile HBSS. The tubes were gently mixed by inverting several times. Ficoll-Paque Plus (15 mL) at room temperature was aliquoted into four 50 mL conical tubes. Then the buffy coat/HBSS mixture (25 mL) was gently and slowly layered on top of the Ficoll-Paque Plus. The samples were centrifuged with Eppendorf Centrifuge 5810R (Rotor A-4-81) at 450 rpm for 35 minutes. The top layer containing plasma was discarded. The interface containing mononuclear cells was transferred into two 50 mL conical tubes. Both conical tubes were filled to total volume of 50 mL with HBSS and centrifuged at 1200 rpm for 10 minutes. The cells were washed again in HBSS and centrifuged at 1000 rpm for 10 minutes. Human red blood cell lysis buffer (5 mL) was added to the cell pellets and incubated for 5 minutes at room temperature. Phosphate buffered saline (45 mL) was added to the conical tubes and centrifuged at 1200 rpm for 10 minutes. The cell pellets were combined and resuspended in 20 mL complete medium and the cells were counted.

Human PBMCs ($1 \times 10^5$ cells) were plated in 96-well plates (PBMCs) in RPMI media containing 10% FBS. Compounds were diluted with DMSO from a 4 mM stock of each compound to obtain different concentrations. Human PBMCs were pretreated with different concentrations of compounds for an hour prior stimulation. Cells were then stimulated with CpG-A ODN 2216 (1 μM) for 18 hours.

The sample with DMSO is labeled as Control E1; the samples with CC-930 (0.1, 0.5 and 10 μM) are labeled as Examples E2-E4 respectively; the samples with Compound (II) (0.1, 0.5 and 5 μM) are labeled as Examples E5-E7 respectively; the samples with Compound (I) (0.5 and 5 μM) are labeled as Examples E8-E9 respectively; the sample with lenalidomide (10 μM) is labeled as Example E10; the sample with thalidomide (10 μM) is labeled as Example E11; the samples with chloroquine (0.5, 1, 5 and 10 μM) are labeled as Examples E12-E15 respectively; the samples with hydroxychloroquine (0.5, 1 and 5 μM) are labeled as Examples E16-E18 respectively; and the samples with quinacrine (0.5 and 5 μM) are labeled as Examples E19-E20 respectively. The samples (Control E1 and Examples E2-E20) contained 1 μM CpG-A.

Supernatant was collected after 18 hours. The IFN-α levels of samples were measured by the IFN-α ELISA obtained from PBL Interferon Source, Piscataway, N.J., known as Human IFN-alpha ELISA Kit. IFN-α levels of samples were assayed by the ELISA according to manufacturer's instructions.

Inhibition of the production of IFN-α by individual compounds were determined in the CpG-A stimulated hPBMC cultures. The concentrations of compounds, including CC-930, Compound (II), Compound (I), lenalidomide, thalidomide, chloroquine, hydroxychloroquine and quinacrine, tested in these experiments were picked around their $C_{max}$ concentrations.

Figure 8:
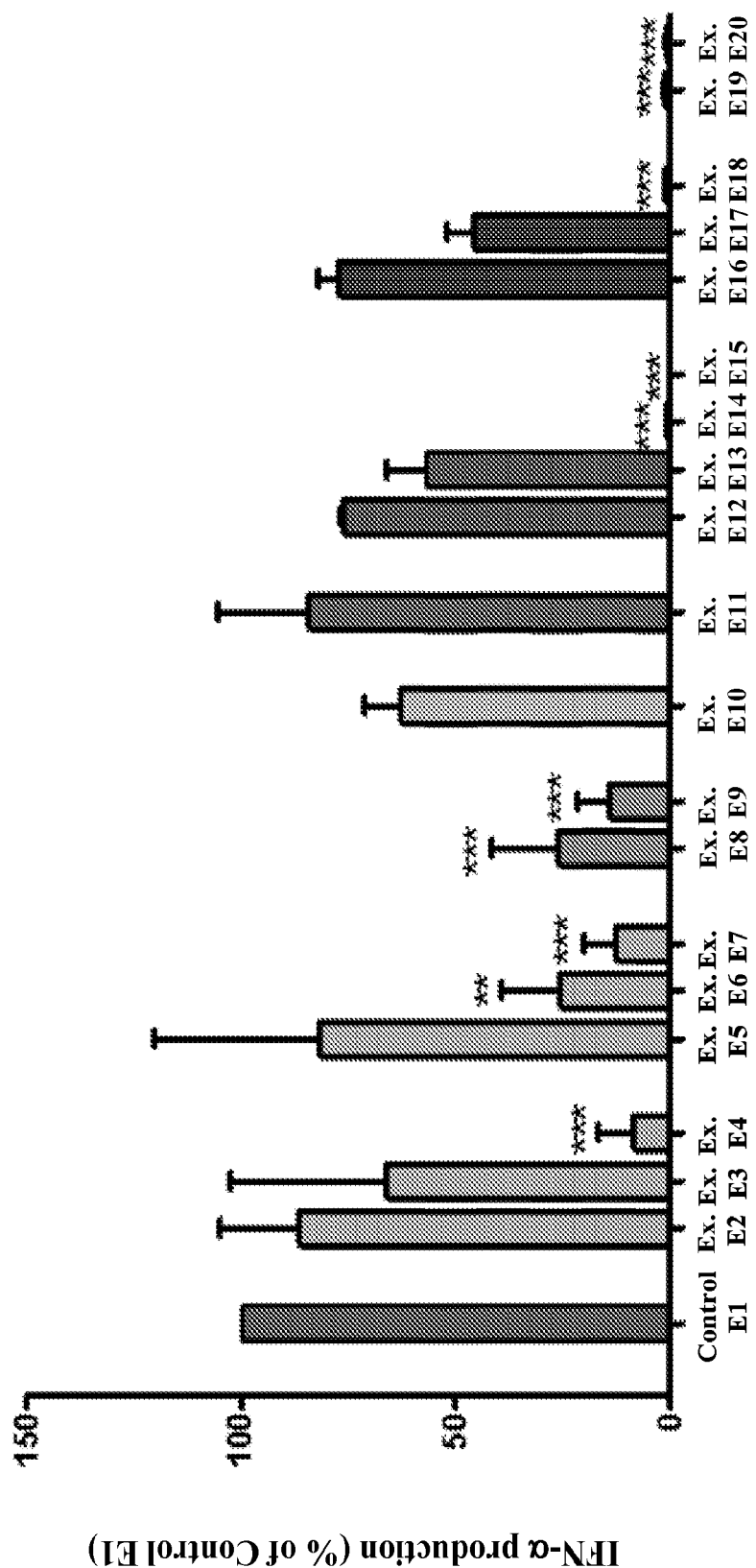
FIG. 8 illustrates the IFN-α production of different samples including Control E1 and Examples E2-E20 used in Example 18.

Referring to FIG. 8, one asterisk * refers to p<0.05; two asterisks  refers to p<0.01; and three asterisks * refers to p<0.0001, as determined by one-way ANOVA followed by Dunnett's multiple comparison post-test comparing the IFN-α levels of samples with the IFN-α level of Control E1.

FIG. 8 shows that Compound (II) and Compound (I) at their $C_{max}$ concentration of 0.5 μM and 5 μM induced a significant inhibition of the production of IFN-α. CC-930 inhibited the production of IFN-α only when the concentration of CC-930 was 10 μM. Lenalidomide and thalidomide (10 μM) did not affect the production of IFN-α. Quinacrine inhibited the production of IFN-α. Chloroquine and hydroxychloroquine induced inhibition of the production of IFN-α only when the concentrations of chloroquine and hydroxychloroquine were 5 μM.

The embodiments described above are intended to be merely exemplary and those skilled in the art will recognize or will be able to ascertain using no more than routine experimentation, numerous equivalents of specific compounds, materials and procedures. All such equivalents are considered to be within the scope of the invention and are encompassed by the appended claims.

What is claimed is:

1. A method of treating alopecia areata in a human, which comprises administering to a patient having alopecia areata a therapeutically effective amount of a compound which is (+)-2-[1-(3-ethoxy-4-methoxyphenyl)-2-methylsulfonylethyl]-4-acetylaminoisoindoline-1,3-dione, or a pharmaceutically acceptable salt or solvate thereof, substantially free of its (−)-enantiomer.

2. A method of treating alopecia areata in a human, which comprises administering to a patient having alopecia areata a pharmaceutical composition comprising a therapeutically effective amount of (+)-2-[1-(3-ethoxy-4-methoxyphenyl)-2-methylsulfonylethyl]-4-acetylaminoisoindoline-1,3-dione, or a pharmaceutically acceptable salt or solvate thereof, substantially free of its (−)-enantiomer.

3. The method of claim 2, wherein the pharmaceutical composition further comprises one or more excipients, diluents or carriers.

4. The method of claim 1, wherein the compound is administered as a pharmaceutically acceptable salt.

5. The method of claim 1, wherein the compound is administered as a pharmaceutically acceptable solvate.

6. The method of claim 5, wherein the solvate is a hydrate.

7. The method of claim 1, further comprising administering to the patient a therapeutically effective amount of a second active agent.

8. The method of claim 7, wherein the second active agent is an anti-inflammatory, an immunomodulatory compound, an anti-malarial, an immunosuppressant, an antibiotic, an antiviral, an immunoglobulin, an immunologic-enhancing drug, a hormone, PGE2 or a combination thereof.

9. The method of claim 8 wherein the second active agent is PGE2.

10. The method of claim 1, wherein the compound or a pharmaceutically acceptable salt or solvate thereof is administered orally in a dosage form of a tablet or a capsule.

11. The method of claim 10, wherein the compound or a pharmaceutically acceptable salt or solvate thereof is administered orally in 5 mg, 10 mg, 15 mg, 20 mg, 25 mg or 30 mg of a tablet or a capsule.

12. The method of claim 1, wherein the therapeutically effective amount is from about 1 mg to about 1000 mg per day.

13. The method of claim 12, wherein the therapeutically effective amount is from about 5 mg to about 500 mg per day.

14. The method of claim 13, wherein the therapeutically effective amount is from about 10 mg to about 200 mg per day.

15. The method of claim 1, wherein the therapeutically effective amount is 20 mg twice per day.

16. The method of claim 1, wherein the therapeutically effective amount is 30 mg twice per day.

17. The method of claim 1, wherein the therapeutically effective amount is 40 mg once per day.

18. The method of claim 1, wherein the compound or a pharmaceutically acceptable salt or solvate thereof is administered once or twice per day.

19. The method of claim 1, wherein the the compound or a pharmaceutically acceptable salt or solvate thereof is administered cyclically.

* * * * *